(12) United States Patent
Noda et al.

(10) Patent No.: US 8,574,911 B2
(45) Date of Patent: Nov. 5, 2013

(54) PRODUCTION AND USE OF YEAST HAVING INCREASED CELLULOSE HYDROLYSIS ABILITY

(75) Inventors: Hideo Noda, Amagasaki (JP); Shohei Kaneko, Amagasaki (JP); Akihiko Kondo, Kobe (JP)

(73) Assignees: Kansai Chemical Engineering Co., Ltd., Amagasaki-shi, Hyogo (JP); Bio-Energy Corporation, Amagasaki-shi, Hyogo (JP)

( * ) Notice: Subject to any disclaimer, the term of this patent is extended or adjusted under 35 U.S.C. 154(b) by 220 days.

(21) Appl. No.: 13/063,225

(22) PCT Filed: Sep. 16, 2009

(86) PCT No.: PCT/JP2009/066193
§ 371 (c)(1),
(2), (4) Date: Apr. 11, 2011

(87) PCT Pub. No.: WO2010/032762
PCT Pub. Date: Mar. 25, 2010

(65) Prior Publication Data
US 2011/0183396 A1 Jul. 28, 2011

(30) Foreign Application Priority Data

Sep. 17, 2008 (JP) ................................ 2008-237887

(51) Int. Cl.
*C12N 15/74* (2006.01)
(52) U.S. Cl.
USPC ............................ 435/483; 435/471; 435/477
(58) Field of Classification Search
None
See application file for complete search history.

(56) References Cited

FOREIGN PATENT DOCUMENTS

| JP | 2006-255676 | 9/2006 |
|---|---|---|
| JP | 2008-086310 | 4/2008 |
| WO | WO 01/79483 | 10/2001 |

OTHER PUBLICATIONS

Daly et al. (Journal of Molecular Recognition, 2005; 18: 119-138).*
Akada et al., "PCR-mediated seamless gene deletion and marker recycling in *Saccharomyces cerevisiae*", *Yeast*, vol. 23, pp. 399-405 (2006).
Fujita et al., "Construction of whole-cell biocatalyst for xylan degradation through cell-surface xylanase display in *Saccharomyces cerevisiae*", *Journal of Molecular Catalysis B: Enzymatic*, vol. 17, pp. 189-195 (2002).
Fujita et al., "Direct and efficient production of ethanol from cellulosic material with a yeast strain displaying cellulolytic enzymes" *Applied and Environmental Microbiology*, vol. 68, No. 10, pp. 5136-5141 (2002).
Fujita et al., "Synergistic saccharification, and direct fermentation to ethanol, of amorphous cellulose by use of an engineered yeast strain codisplaying three types of cellulolytic enzyme" *Applied and Environmental Microbiology*, vol. 70, No. 2, pp. 1207-1212 (2004).
Katahira et al., "Construction of a xylan-fermenting yeast strain through codisplay of xylanolytic enzymes on the surface of sylose-utilizing *Saccharomyces cerevisiae* cells" *Applied and Environmental Microbiology*, vol. 70, No. 9, pp. 5407-5414 (2004).
Katahira et al., "Ethanol fermentation from lignocellulosic hydrolystate by a recombinant xylose- and cellooligosaccharide-assimilating yeast strain" *Appl. Microbiol. Biotechnol.* vol. 72, pp. 1136-1143 (2006).
Lipke et al., "Aga1 is the structurasl gene for *Saccharomyces cerevisiae* a-agglutinin, a cell surface glycoprotien involved in cell-cell interactions during mating" *Molecular and Cellular Biology*, vol. 9, No. 8, pp. 3155-3165 (1989).
Matsumoto et al., "Construction of yeast strains with high cell surface lipase activity by using novel display systems based on the Flo1p flocculation functional domain", *Applied and Environmental Microbiology*, vol. 68, No. 9, pp. 4517-4522 (2002).
Okada et al., "Expression of two *Trichoderma reesei* xylanases in the fission yeast *Schizosaccharomyces pombe*", *Journal of Bioscience and Bioengineering*, vol. 88, No. 5, pp. 563-566 (1999).
Sato et al., "Long anchor using Flo1 protein enhances reactivity of cell surface-displayed glucoamylase to polymer substrates", *Appl. Microbiol. Biotechnol.*, vol. 60, pp. 469-474 (2002).
Takahashi et al., "Function of the prosequence for in vivo folding and secretion of active *Rhizopus oryzae* lipase in *Saccharomyces cerevisiae*" *Appl. Microbiol. Biotechnol.*, vol. 55, pp. 454-462 (2001).
Tanaka et al., "Saibo Hyoso Teiji Gijutsu o Mochiita Biseibutsu no Kokinoka to Yuyo Bussitsu Seisan" *Bio Industry*, vol. 25, No. 8, pp. 13-20, (2008).
Yanase et al., "Cellulase Hatsugen Kobo ni yoru Cellulose kara no Bioethanol Seisan" *Abstracts of Autumn Meeting of the Society of Chemical Engineers*, vol. 40, p. X160 (2008).
International Preliminary Report on Patentability and Written Opinion of the International Searching Authority in PCT/JP2009/066193, Dated Nov. 3, 2009.
Toshiyuk Murai et al., "Assimilation of Cellooligosaccharides by a Cell Surface-Engineered Yeast Expressing β-Glucosidase and Carboxymethylcellulase from *Aspergillus aculeatus*"; Applied and Environmental Microbiology, Dec. 1998, p. 4857-4861 (5 pages).

* cited by examiner

*Primary Examiner* — Suzanne M Noakes
*Assistant Examiner* — Jae W Lee
(74) *Attorney, Agent, or Firm* — Alchemy-Partners, PC

(57) ABSTRACT

The present invention provides a method for producing an yeast having an increased cellulose hydrolysis ability. The method includes the step of introducing increased integration copy numbers of both a gene for an enzyme capable of hydrolyzing crystalline cellulose and a gene for an enzyme capable of hydrolyzing noncrystalline cellulose into a noncellulolytic yeast to give a transformed yeast. The yeast having an increased cellulose hydrolysis ability can be suitably used for ethanol production from cellulose-based materials.

7 Claims, 9 Drawing Sheets

```
                       SEQUENCE LISTING

<160> NUMBER OF SEQ ID NOS: 32

<210> SEQ ID NO 1
<211> LENGTH: 22
<212> TYPE: DNA
<213> ORGANISM: Artificial
<220> FEATURE:
<223> OTHER INFORMATION: Primer for URA3 delete

<400> SEQUENCE: 1
ggagaatcca tacaagaaat cg                                          22

<210> SEQ ID NO 2
<211> LENGTH: 26
<212> TYPE: DNA
<213> ORGANISM: Artificial
<220> FEATURE:
<223> OTHER INFORMATION: Primer for URA3 delta r

<400> SEQUENCE: 2
gtaaaatact gttacttggt tctggc                                      26

<210> SEQ ID NO 3
<211> LENGTH: 24
<212> TYPE: DNA
<213> ORGANISM: Artificial
<220> FEATURE:
<223> OTHER INFORMATION: Primer HIS3-Green U

<400> SEQUENCE: 3
caggcaagat aaacgaaggc aaag                                        24

<210> SEQ ID NO 4
<211> LENGTH: 25
<212> TYPE: DNA
<213> ORGANISM: Artificial
<220> FEATURE:
<223> OTHER INFORMATION: Primer HIS3-Green R

<400> SEQUENCE: 4
cactacggtg atgatcattc ttgcc                                       25

<210> SEQ ID NO 5
<211> LENGTH: 82
<212> TYPE: DNA
<213> ORGANISM: Artificial
<220> FEATURE:
<223> OTHER INFORMATION: Primer URA3 fragment

<400> SEQUENCE: 5
ggcaagaatg atcatcaccg tagtgatcat tctatacgtg tcattctgaa cgaggcgcgc  60
tttccgattc ggtaatctcc ga                                          82

<210> SEQ ID NO 6
```

```
<211> LENGTH: 60
<212> TYPE: DNA
<213> ORGANISM: Artificial
<220> FEATURE:
<223> OTHER INFORMATION: Primer HIS3-40Uc

<400> SEQUENCE: 6
gcattacctt gtcatcttca gtatcatact gttcgtatac gggtaataac tgatataatt      60

<210> SEQ ID NO 7
<211> LENGTH: 27
<212> TYPE: DNA
<213> ORGANISM: Artificial
<220> FEATURE:
<223> OTHER INFORMATION: Primer TRP1-988

<400> SEQUENCE: 7
ctattagctg aattgccact gctatcg                                          27

<210> SEQ ID NO 8
<211> LENGTH: 21
<212> TYPE: DNA
<213> ORGANISM: Artificial
<220> FEATURE:
<223> OTHER INFORMATION: Primer TRP1-28r

<400> SEQUENCE: 8
gctgcctttg tgtgcttaat c                                                21

<210> SEQ ID NO 9
<211> LENGTH: 78
<212> TYPE: DNA
<213> ORGANISM: Artificial
<220> FEATURE:
<223> OTHER INFORMATION: Primer TRP1-URA3

<400> SEQUENCE: 9
gattaagcac acaaaggcag cgcaggcctt ttgaaaagca agcataaaag atctaaacat      60
agattcggta atctccga                                                   78

<210> SEQ ID NO 10
<211> LENGTH: 60
<212> TYPE: DNA
<213> ORGANISM: Artificial
<220> FEATURE:
<223> OTHER INFORMATION: Primer TRP1-40r

<400> SEQUENCE: 10
aggcaagtgc acaaacaata cttaaataaa tactactcag gggtaataac tgatataatt      60

<210> SEQ ID NO 11
<211> LENGTH: 20
<212> TYPE: DNA
<213> ORGANISM: Artificial
<220> FEATURE:
<223> OTHER INFORMATION: Primer LEU2-UP 3rd

<400> SEQUENCE: 11
gtctgcccct aagaagatcg                                                  20

<210> SEQ ID NO 12
<211> LENGTH: 21
<212> TYPE: DNA
<213> ORGANISM: Artificial
<220> FEATURE:
<223> OTHER INFORMATION: Primer LEU2-down 3rd
```

<400> SEQUENCE: 12
cggatgcaaa gttacatggt c                                       21

<210> SEQ ID NO 13
<211> LENGTH: 78
<212> TYPE: DNA
<213> ORGANISM: Artificial
<220> FEATURE:
<223> OTHER INFORMATION: Primer LEU2-URA3 3rd

<400> SEQUENCE: 13
gaccatgtaa ctttgcatcc ggacaaggag gagggcacca cacaaaaagt taggtgtaac    60
agattcggta atctccga                                           78

<210> SEQ ID NO 14
<211> LENGTH: 60
<212> TYPE: DNA
<213> ORGANISM: Artificial
<220> FEATURE:
<223> OTHER INFORMATION: Primer LEU2-40r

<400> SEQUENCE: 14
aatattaatg ttaaagtgca attcttttc cttatcacgt gggtaataac tgatataatt    60

<210> SEQ ID NO 15
<211> LENGTH: 37
<212> TYPE: DNA
<213> ORGANISM: Artificial
<220> FEATURE:
<223> OTHER INFORMATION: Primer EG NheI Fw

<400> SEQUENCE: 15
ctagctagca tgcaactgtt caatttgcca ttgaaag                      37

<210> SEQ ID NO 16
<211> LENGTH: 44
<212> TYPE: DNA
<213> ORGANISM: Artificial
<220> FEATURE:
<223> OTHER INFORMATION: Primer EG XmaI Rev

<400> SEQUENCE: 16
tcccccgggg tttgattatg ttctttctat ttgaatgaga tatg              44

<210> SEQ ID NO 17
<211> LENGTH: 30
<212> TYPE: DNA
<213> ORGANISM: Artificial
<220> FEATURE:
<223> OTHER INFORMATION: Primer 1 for PGK promoter

<400> SEQUENCE: 17
ttttctcgag aaagatgccg atttgggcgc                              30

<210> SEQ ID NO 18
<211> LENGTH: 30
<212> TYPE: DNA
<213> ORGANISM: Artificial
<220> FEATURE:
<223> OTHER INFORMATION: Primer 2 for PGK promoter

<400> SEQUENCE: 18
gcccgctagc gttttatatt tgttgtaaaa                              30

<210> SEQ ID NO 19

```
<211> LENGTH: 30
<212> TYPE: DNA
<213> ORGANISM: Artificial
<220> FEATURE:
<223> OTHER INFORMATION: Primer 1 for PGK terminater

<400> SEQUENCE: 19
gcccagatct gaaataaatt gaattgaatt                                  30

<210> SEQ ID NO 20
<211> LENGTH: 30
<212> TYPE: DNA
<213> ORGANISM: Artificial
<220> FEATURE:
<223> OTHER INFORMATION: Primer 2 for PGK terminater

<400> SEQUENCE: 20
ttttgcggcc gcagctttaa cgaacgcaga                                  30

<210> SEQ ID NO 21
<211> LENGTH: 52
<212> TYPE: DNA
<213> ORGANISM: Artificial
<220> FEATURE:
<223> OTHER INFORMATION: Primer 1 for multi-cloning site

<400> SEQUENCE: 21
ttttgctagc gtcgacacta gtggatcccc cgggtctaga gaattcagat ct         52

<210> SEQ ID NO 22
<211> LENGTH: 52
<212> TYPE: DNA
<213> ORGANISM: Artificial
<220> FEATURE:
<223> OTHER INFORMATION: Primer 2 for multi-cloning site

<400> SEQUENCE: 22
ttttagatct gaattctcta gacccggggg atccactagt gtcgacgcta gc         52

<210> SEQ ID NO 23
<211> LENGTH: 42
<212> TYPE: DNA
<213> ORGANISM: Artificial
<220> FEATURE:
<223> OTHER INFORMATION: Primer 1 for GAPDH terminater

<400> SEQUENCE: 23
aaggaaaaaa gcggccgcac cagttctcac acggaacacc ac                    42

<210> SEQ ID NO 24
<211> LENGTH: 51
<212> TYPE: DNA
<213> ORGANISM: Artificial
<220> FEATURE:
<223> OTHER INFORMATION: Primer 2 for GAPDH terminater

<400> SEQUENCE: 24
aaggaaaaaa gcggccgctc aatcaatgaa tcgaaaatgt cattaaaata g          51

<210> SEQ ID NO 25
<211> LENGTH: 40
<212> TYPE: DNA
<213> ORGANISM: Artificial
<220> FEATURE:
<223> OTHER INFORMATION: Primer XYL2c-XhoI(F)

<400> SEQUENCE: 25
```
ccgctcgaga ccagttctca cacggaacac cactaatgga                       40

<210> SEQ ID NO 26
<211> LENGTH: 45
<212> TYPE: DNA
<213> ORGANISM: Artificial
<220> FEATURE:
<223> OTHER INFORMATION: Primer XYL2c-NotI(R)

<400> SEQUENCE: 26
atagtttagc ggccgctcaa tcaatgaatc gaaaatgtca ttaaa                 45

<210> SEQ ID NO 27
<211> LENGTH: 40
<212> TYPE: DNA
<213> ORGANISM: Artificial
<220> FEATURE:
<223> OTHER INFORMATION: bgl1 primer 1

<400> SEQUENCE: 27
gatctccatg gctgatgaac tggcgttctc tcctcctttc                       40

<210> SEQ ID NO 28
<211> LENGTH: 40
<212> TYPE: DNA
<213> ORGANISM: Artificial
<220> FEATURE:
<223> OTHER INFORMATION: bgl1 primer 2

<400> SEQUENCE: 28
tggcgctcga gccttgcacc ttcgggagcg ccgcgtgaag                       40

<210> SEQ ID NO 29
<211> LENGTH: 111
<212> TYPE: DNA
<213> ORGANISM: Artificial
<220> FEATURE:
<223> OTHER INFORMATION: Primer ss EGII forward

<400> SEQUENCE: 29
tcccccggga tgcaactgtt caatttgcca ttgaaagttt cattctttct cgtcctctct    60
tactttcctt tgctcgtttc tcagcagact gtctggggcc agtgtggagg t            111

<210> SEQ ID NO 30
<211> LENGTH: 40
<212> TYPE: DNA
<213> ORGANISM: Artificial
<220> FEATURE:
<223> OTHER INFORMATION: Primer ss EGII reverse

<400> SEQUENCE: 30
tcccccgggc tactttcttg cgagacacga gctgaccaag                       40

<210> SEQ ID NO 31
<211> LENGTH: 110
<212> TYPE: DNA
<213> ORGANISM: Artificial
<220> FEATURE:
<223> OTHER INFORMATION: Primer ss CBH2 forward

<400> SEQUENCE: 31
tcccccggga tgcaactgtt caatttgcca ttgaaagttt cattctttct cgtcctctct    60
tactttcctt tgctcgtttc tcaagcttgc tcaagcgtct ggggccaatg             110

<210> SEQ ID NO 32

```
<211> LENGTH: 46
<212> TYPE: DNA
<213> ORGANISM: Artificial
<220> FEATURE:
<223> OTHER INFORMATION: Primer ss CBH2 reverse

<400> SEQUENCE: 32
tcccccgggt tacaggaacg atgggtttgc gtttgtgaga agctgc              46
```

PRODUCTION AND USE OF YEAST HAVING INCREASED CELLULOSE HYDROLYSIS ABILITY

TECHNICAL FIELD

The present invention relates to the production and use of an yeast having an increased cellulose hydrolysis ability.

BACKGROUND ART

In recent years, increased production of biofuel from edible grain (for example, corn, potato, and sugar cane) has led to high food prices, and it is thus urgently necessary to produce ethanol from non-edible carbon source soft biomass (for example, rice straw, wheat straw, bagasse, rice husk, cotton, bamboo, paper, corn stover, or other wastes).

It has been proposed that an acid treatment or a supercritical treatment is made on biomass containing cellulose or hemicellulose to prepare from the source material glucose which microorganisms can utilize for fermentation.

Conventional methods for producing glucose from a cellulose-based material include acid saccharification methods and enzyme saccharification methods. Regarding acid saccharification methods, it has been known a dilute acid saccharification method for saccharifying a cellulose-based material with a dilute acid at high temperatures (200° C. or greater) as well as a method of saccharifying a cellulose-based material with concentrated sulfuric acid or the like. However, in either method, a cellulose-based material is hydrolysed under severe conditions, which results in a degraded product, glucose, from the cellulose-based material and a subsequent secondary reaction of degrading the glucose. Thus, yield of saccharification is as poor as about 50%, and the product of the reaction of degrading the glucose needs to be removed from the saccharified solution. There are some problems in use of the saccharified solution without removal of the product of the reaction of degrading the glucose, as a carbon source for fermentation.

Meanwhile, the enzyme saccharification method allows the saccharification of a cellulosic material under mild conditions, which results in a lower rate of reaction for saccharification, and thus it is problematic in that it takes a longer period of time for sufficient saccharification. In addition, it is problematic also in higher enzyme costs since the method requires larger amounts of enzyme for sufficient saccharification due to the lower titer of commercially available enzymes for use in saccharification.

An attempt has been made to modify microorganisms which originally cannot utilize the principal components, such as cellulose and hemicellulose, of soft biomass for fermentation, using bioengineering techniques to attain direct ethanol fermentation from the non-edible carbon sources. As such bioengineering techniques, cell surface-displaying techniques are suitably used. For example, yeasts that display on the surface a group of cellulolytic enzymes have been created by cell surface-displaying techniques (Patent Documents 1 and 2). Although the yeast *Saccharomyces cerevisiae* cannot metabolize xylose, *Saccharomyces cerevisiae* that displays on the cell surface xylan-degrading enzymes xylanase 2 (XYNII) from *Trichoderma reesei* and β-xylosidase (XylA) from *Aspergillus oryzae* and that expresses a xylose reductase (XR) gene and a xylitol dehydrogenase (XDH) gene (both from *Pichia stipitis*) and a xylulokinase (XK) gene (from *Saccharomyces cerevisiae*) has been created, and attempted to produce ethanol from xylan in birch trees (Non-Patent Document 1).

However, further research is required in view of industrial usefulness. The biomass of cellulose has a crystalline portion and a noncrystalline portion. The enzymatic hydrolytic reaction is easier on the noncrystalline portion than on the crystalline portion. It is thought that the rate of hydrolysis is lower on the crystalline portion which has rigid intramolecular and intermolecular hydrogen bonds. It is important to more efficiently carry out the hydrolysis of cellulose which has such a complex configuration.

PRIOR ART DOCUMENTS

Patent Documents

Patent Document 1: WO 01/79483
Patent Document 2: Japanese Laid-Open Patent Publication No. 2008-86310
Patent Document 3: Japanese Laid-Open Patent Publication No. 2006-255676

Non-Patent Documents

Non-Patent Document 1: S. Katahira et al., *Applied and Environmental Microbiology* 2004, vol. 70, pp. 5407-5414
Non-Patent Document 2: *Appl. Microbiol. Biotech.*, 2002, vol. 60, pp. 469-474
Non-Patent Document 3: *Applied and Environmental Microbiology* 2002, vol. 68, pp. 4517-4522
Non-Patent Document 4: R. Akada et al., *Yeast*, 2006, vol. 23, pp. 399-405
Non-Patent Document 5: H. Okada et al., *J. Biosci Bioeng.*, 1999, vol. 88, p. 563
Non-Patent Document 6: Y. Fujita et al., *Journal of molecular Catalysis B. Enzymatic*, 2002, vol. 17, pp. 189-195
Non-Patent Document 7: S. Katahira et al., *Appl. Microbiol. Biotechnol.*, 2006, vol. 72, pp. 1136-43
Non-Patent Document 8: Rose et al., *Methods in Yeast Genetics, A Laboratory Course Manual*, Cold Spring Harbor Laboratory Press: Cold Spring Harbor, N.Y., 1990
Non-Patent Document 9: P. N. Lipke et al., *Mol. Cell. Biol.*, August 1989, 9(8), pp. 3155-65
Non-Patent Document 10: Y. Fujita et al., *Applied and Environmental Microbiology* 2002, vol. 68, pp. 5136-41
Non-Patent Document 11: Y. Fujita et al., *Applied and Environmental Microbiology* 2004, vol. 70, pp. 1207-12
Non-Patent Document 12: Takahashi et al., *Appl. Microbiol. Biotechnol.*, 2001, vol. 55, pp. 454-462
Non-Patent Document 13: C. S. Walseth, *Tech. Assoc. Pulp Paper Ind.*, 1952, Vol. 35, pp. 228-233

SUMMARY OF INVENTION

Problems to be Solved by the Invention

It is an object of the present invention to provide an yeast having a strong cellulose hydrolysis ability. Furthermore, it is an object of the present invention to provide an efficient method for producing ethanol from a cellulose-based material.

Means for Solving the Problems

The invention provides a method for producing an yeast having an increased cellulose hydrolysis ability, comprising:
 introducing a group of genes for enzymes capable of hydrolyzing cellulose into a noncellulolytic yeast to give a transformed yeast, wherein the group of genes comprises a gene for an enzyme capable of hydrolyzing crystalline cellulose and a gene for an enzyme capable of hydrolyzing noncrystalline cellulose, wherein increased integration copy numbers of both the gene for the enzyme capable of hydrolyzing crystalline cellulose and the gene for the enzyme capable of hydrolyzing noncrystalline cellulose are introduced.

In an embodiment, the enzyme capable of hydrolyzing crystalline cellulose is cellobiohydrolase and the enzyme capable of hydrolyzing noncrystalline cellulose is endoglucanase.

In another embodiment, the introduction into the noncellulolytic yeast is performed such that at least one of the enzyme capable of hydrolyzing crystalline cellulose and the enzyme capable of hydrolyzing noncrystalline cellulose is surface-displayed.

In a further other embodiment, the group of genes for enzymes capable of hydrolyzing cellulose further comprises a gene for an enzyme capable of hydrolyzing cellobiose or cello-oligosaccharide.

In a further embodiment, the integration copy number of each of the gene for the enzyme capable of hydrolyzing crystalline cellulose and the gene for the enzyme capable of hydrolyzing noncrystalline cellulose is at least two copies relative to one copy of the integration copy number of the gene for the enzyme capable of hydrolyzing cellobiose or cello-oligosaccharide.

In a further embodiment, the enzyme capable of hydrolyzing cellobiose or cello-oligosaccharide is β-glucosidase.

In a further embodiment, the introduction into the noncellulolytic yeast is performed such that the enzyme capable of hydrolyzing cellobiose or cello-oligosaccharide is surface-displayed.

The invention further provides an yeast having an increased cellulose hydrolysis ability obtained according to the method as mentioned above.

The invention also provides an yeast having an increased cellulose hydrolysis ability, having a gene for cellobiohydrolase, a gene for endoglucanase, and a gene for β-glucosidase, wherein each of the gene for the cellobiohydrolase and the gene for the endoglucanase is integrated in at least two copies relative to one copy of the gene for the β-glucosidase.

In an embodiment, the cellobiohydrolase, the endoglucanase, and the β-glucosidase are surface-displayed Furthermore, the invention provides a method for producing ethanol, comprising:

reacting a cellulose-based material with the yeast having an increased cellulose hydrolysis ability as mentioned above to produce ethanol.

Effects of Invention

According to the invention, it is provided that an yeast having an increased cellulose hydrolysis ability. With the yeast having an increased cellulose hydrolysis ability, the amount of ethanol produced directly from cellulose can be increased. Moreover, it is provided that an efficient and cost-effective method for producing ethanol from a cellulose-based material using the yeast having an increased cellulose hydrolysis ability.

Figure 1:
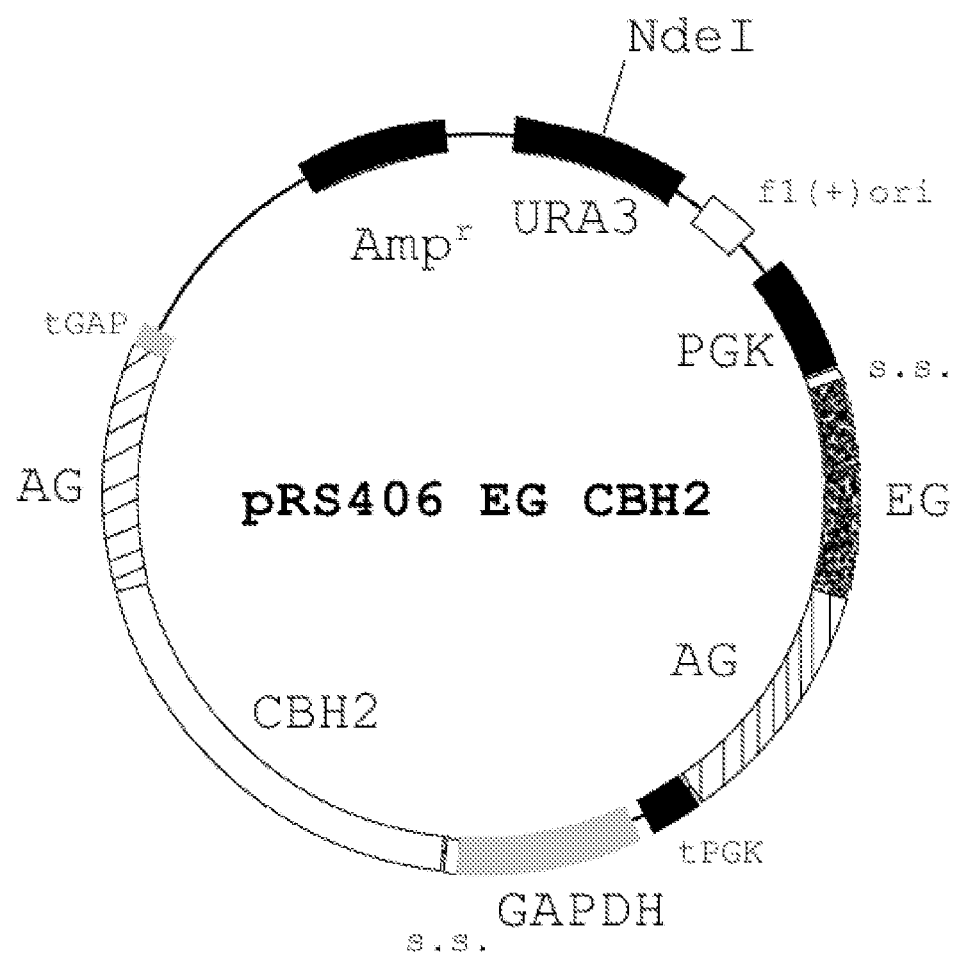
FIG. 1 is a schematic drawing of a plasmid pRS406 EG CBH2.

MODE FOR CARRYING OUT THE INVENTION (Yeast Having Increased Cellulose Hydrolysis Ability and Production Thereof)

In the present invention, an yeast (such as a wild-type yeast) originally having no or little cellulose hydrolysis ability (herein, which may be also referred to as a "noncellulolytic yeast") is genetically modified to express a group of cellulolytic enzymes, thereby giving a transformed yeast having an enhanced cellulose hydrolysis ability.

An enzyme capable of hydrolyzing cellulose, i.e., cellulolytic enzyme, may be derived from any cellulolytic enzyme-producing microorganisms. Typical examples of cellulolytic enzyme-producing microorganisms include those belonging to the genus *Aspergillus* (for example, *Aspergillus aculeatus, Aspergillus niger*, and *Aspergillus oryzae*), the genus *Trichoderma* (for example, *Trichoderma reesei*), the genus *Clostridium* (for example, *Clostridium thermocellum*), the genus *Cellulomonas* (for example, *Cellulomonas fimi* and *Cellulomonas uda*), the genus *Pseudomonas* (for example, *Pseudomonas fluorescence*), and the like.

The cellulolytic enzymes may be enzymes capable of cleaving β1,4-glucosidic linkage. Typical examples of enzymes capable of cleaving β1,4-glucosidic linkage include, but are not limited to, endo-β1,4-glucanase (hereinafter simply referred to as "endoglucanase"), cellobiohydrolase, and β-glucosidase.

Endoglucanase is usually referred to also as cellulase and can cleave cellulose intramolecularly ("intramolecular cellulose cleaving") to generate glucose, cellobiose, and cello-oligosaccharide (the degree of polymerization may be 3 or greater and usually 10 or less but it is not limited thereto). Endoglucanase is highly reactive toward cellulose having a low degree of crystallization or noncrystalline cellulose such as amorphous cellulose, soluble cello-oligosaccharide, and carboxymethylcellulose (CMC) and other cellulose derivatives, but is poorly reactive toward cellulose microfibril, which has a crystalline structure. Endoglucanase is a typical example of an enzyme capable of hydrolyzing noncrystalline cellulose (hereinafter also referred to as a "noncrystalline cellulose hydrolyzable enzyme"). There are five kinds of endoglucanase, which are referred to as endoglucanase I, endoglucanase II, endoglucanase III, endoglucanase IV, and endoglucanase V, respectively, and distinguished by the difference in amino acid sequence but have in common an action of intramolecular cellulose cleaving. For example, endoglucanase derived from *Trichoderma reesei* (especially EGII) may be used, but endoglucanase is not limited thereto.

Cellobiohydrolase can degrade cellulose from either the reducing terminal or the nonreducing terminal thereof to release cellobiose ("cellulose molecule terminal cleaving"). Cellobiohydrolase can degrade crystalline cellulose such as cellulose microfibril, which has a crystalline structure, but is poorly reactive toward cellulose having a low degree of crystallization or noncrystalline cellulose such as carboxymethylcellulose (CMC) and other cellulose derivatives. Cellobiohydrolase is a typical example of an enzyme capable of hydrolyzing crystalline cellulose (hereinafter also referred to as a "crystalline cellulose hydrolyzable enzyme"). Due to the rigid structure of crystalline cellulose with the dense intermolecular and intramolecular hydrogen bonding, the hydrolysis of crystalline cellulose by cellobiohydrolase may be slower than the hydrolysis of noncrystalline cellulose by endoglucanase. There are two kinds of cellobiohydrolase, which are referred to as cellobiohydrolase 1 and cellobiohydrolase 2, respectively, and distinguished by the difference in amino acid sequence but have in common an action of cellulose molecule terminal cleaving. For example, cellobiohydrolase derived from *Trichoderma reesei*(especially CBH2) may be used, but cellobiohydrolase is not limited thereto.

β-Glucosidase is an exo-hydrolase, which releases glucose units from the nonreducing end in cellulose. β-Glucosidase can cleave the β1,4-glucosidic linkage between aglycon or a sugar chain and β-D-glucose, and hydrolyze cellobiose or cello-oligosaccharide to generate glucose. β-Glucosidase is a typical example of an enzyme capable of hydrolyzing cellobiose or cello-oligosaccharide. There is currently one kind of β-glucosidase known, which is called β-glucosidase 1. For example, β-glucosidase derived from *Aspergillus aculeatus* (especially BGL1) may be used, but β-glucosidase is not limited thereto.

In the present invention, as described in detail below, a transformed yeast may be produced by introducing a group of genes for cellulolytic enzymes. The group of genes for cellulolytic enzymes includes a gene for an enzyme capable of hydrolyzing crystalline cellulose and a gene for an enzyme capable of hydrolyzing noncrystalline cellulose. The enzyme capable of hydrolyzing crystalline cellulose ("crystalline cellulose hydrolyzable enzyme") refers to any enzyme that can hydrolyze cellulose that has a crystalline structure such as microfibril, and an example may be, but is not limited to, cellobiohydrolase. The enzyme capable of hydrolyzing noncrystalline cellulose ("noncrystalline cellulose hydrolyzable enzyme") refers to any enzyme that can hydrolyze the chain of cellulose having a low degree of crystallization or of noncrystalline cellulose such as amorphous cellulose although not hydrolyze cellulose having a crystalline structure, and an example may be, but is not limited to, endoglucanase. Preferably, the group of genes for enzymes capable of hydrolyzing cellulose further includes a gene for an enzyme capable of hydrolyzing cellobiose or cello-oligosaccharide. Cello-oligosaccharide is as described above. An example of an enzyme capable of hydrolyzing cellobiose or cello-oligosaccharide may be, but is not limited to, β-glucosidase.

In the present invention, a transformed yeast may be produced by genetically modifying a noncellulolytic yeast (such as wild-type yeast) such that expression levels of both a crystalline cellulose hydrolyzable enzyme and a noncrystalline cellulose hydrolyzable enzyme are increased. That is, increased integration copy numbers of both the genes for the respective enzymes are introduced into a noncellulolytic yeast to give a transformed yeast. The manner of expression of the crystalline cellulose hydrolyzable enzyme and the noncrystalline cellulose hydrolyzable enzyme is not limited as long as the expressed enzymes act on a cellulosic substrate.

For example, the manner of expression may be surface display or secretory expression. At least one or both of the crystalline cellulose hydrolyzable enzyme and the noncrystalline cellulose hydrolyzable enzyme may be either surface-displayed or secreted. An yeast may be transformed such that the surface display and the secretion of the crystalline cellulose hydrolyzable enzyme and the noncrystalline cellulose hydrolyzable enzyme occur together.

It is preferable that the gene for an enzyme capable of hydrolyzing cellobiose or cello-oligosaccharide is integrated in the transformed yeast, which may enhance the glucose production from cellulose. This enzyme may also be surface-displayed or secreted, and preferably it is surface-displayed. To more efficiently perform ethanol fermentation from cellulose, it is preferable that an enzyme capable of hydrolyzing cellobiose or cello-oligosaccharide is also expressed on the yeast.

The integration copy number of each of the gene for the crystalline cellulose hydrolyzable enzyme and the gene for the noncrystalline cellulose hydrolyzable enzyme may be at least two copies relative to one copy of the integration copy number of the gene for the enzyme capable of hydrolyzing cellobiose or cello-oligosaccharide.

In an example, cellobiohydrolase may be used as a crystalline cellulose hydrolyzable enzyme, and endoglucanase may be used as a noncrystalline cellulose hydrolyzable enzyme. To increase the expression of both enzymes, a single yeast may be transformed with at least two vectors which contain together expression cassettes (described in detail below) of genes for these enzymes. A single yeast may be transformed with at least two pairs of the combination of vectors each of which contains an expression cassette of one of genes for these enzymes. When an industrial yeast, which does not have any auxotrophic marker originally, is to be transformed, it is desirable to provide it with an auxotrophic marker, and it is thus preferable in terms of operational efficiency to prepare a vector (examples of vectors include those described in the examples below) containing an auxotrophic marker together with expression cassettes of the genes for these enzymes, as described in detail below.

The transformed yeast may further contain β-glucosidase integrated as an enzyme capable of hydrolyzing cellobiose or cello-oligosaccharide.

The production of ethanol may be enhanced by increasing the integration copy numbers of cellobiohydrolase and endoglucanase relative to the integration copy number of β-glucosidase gene. Therefore, at least two copies of each of the genes for the cellobiohydrolase and the endoglucanase may be integrated relative to one copy of the integration copy number of the gene for the β-glucosidase. Three or more copies of each of the genes for the cellobiohydrolase and the endoglucanase may be integrated relative to one copy of the integration copy number of the gene for the β-glucosidase. By genetically modifying a noncellulolytic yeast (such as a wild-type yeast) in such a way, it is possible to obtain an yeast having increased production of ethanol.

In one embodiment, the genes are integrated such that at least one or both of the cellobiohydrolase and the endoglucanase are either surface-displayed or secreted and the β-glucosidase is surface-displayed. Preferably, the cellobiohydrolase, the endoglucanase, and the β-glucosidase may be surface-displayed.

A transformed yeast obtained as described above is provided and enhanced with a cellulose hydrolysis ability. Herein, such a transformed yeast with provided and enhanced cellulose hydrolysis ability may also be referred to as a "yeast having an increased cellulose hydrolysis ability".

Hereinafter, preparation of an yeast having an increased cellulose hydrolysis ability (i.e., preparation of a transformed yeast) will be described, but the present invention is not limited thereto.

The gene of an enzyme to be expressed can be obtained from a microorganism that produces the enzyme by PCR or hybridization with primers or a probe designed based on known sequence information.

The enzyme gene can be used to construct an expression cassette. The expression cassette may contain so-called regulatory factors such as an operator, a promoter, a terminator, and an enhancer that regulate the expression of the gene. The promoter and the terminator may be those of the gene to be expressed, or those derived from a different gene may be used. For the promoter and the terminator, promoters and terminators of GAPDH (glyceraldehyde 3'-phosphate dehydrogenase), PGK (phosphoglycerate kinase), GAP (glyceraldehyde 3'-phosphate), and like may be used, but the selection of a promoter and a terminator may depend on the expression of the enzyme gene of interest and they can be suitably selected by those skilled in the art. Additional factors that regulate the expression (such as an operator and an enhancer) or the like may be contained as necessary. Expression regulatory factors such as operators and enhancers may also be suitably selected by those skilled in the art. The expression cassette may further contain a necessary functional sequence depending on the purpose of the expression of the gene. The expression cassette may contain linkers as necessary.

For the expression of an enzyme for yeast surface display, a cell surface engineering technique may be used. Examples include, although they are not limited to, (a) displaying an enzyme on the cell surface via the GPI anchor of a cell surface-localized protein, (b) displaying an enzyme on the cell surface via the sugar chain binding domain of a cell surface-localized protein, and (c) displaying an enzyme on the cell surface via a periplasm protein (another receptor molecule or target receptor molecule). Relevant techniques for cell surface engineering are described also in, for example, Patent Documents 1 and 2.

Examples of usable cell surface-localized proteins include α- or a-agglutinin, which is an yeast flocculation protein (for use as the GPI anchor); Flo1 proteins (Flo1 proteins can be used as the GPI anchor with modification of amino acid length on the N-terminal; for example, Flo42, Flo102, Flo146, Flo318, Flo428, and the like; Non-Patent Document 2: Note that Flo1326 refers to the full-length Flo1 protein); Flo proteins (there are no GPI anchor functions and flocculability is used, Floshort or Flolong; Non-Patent Document 3); invertase, which is a periplasm-localized protein (no GPI anchor is used); and the like.

First, (a) use of GPI anchor is described. The gene coding for a protein localized on a cell surface by a GPI anchor has, in order from the N-terminal, a gene coding for a secretion signal sequence, a gene coding for a cell surface-localized protein (a sugar chain binding protein domain), and a gene coding for a GPI anchor attachment recognition signal sequence. A cell surface-localized protein (a sugar chain binding protein) expressed from this gene in a cell is directed outside the cell membrane by a secretion signal, and then a GPI anchor attachment recognition signal sequence binds to the GPI anchor of the cell membrane via a specifically truncated C-terminal portion to immobilize the protein on the cell membrane. Subsequently, the protein is cleaved near the root of the GPI anchor by PI-PLC, and integrated into the cell wall, and immobilized on the cell surface, resulting in display of the protein on the cell surface.

Here, the secretion signal sequence refers to an amino acid sequence rich in highly hydrophobic amino acids, that is linked to the N terminal of a protein that is generally secreted outside the cell, including the periplasm, i.e., secretory protein, and is usually eliminated when the secretory protein is secreted from inside the cell through the cell membrane to the outside the cell. Any secretion signal sequence may be used irrespective of its origin as long as the secretion signal sequence can direct the expression product to the cell membrane. For example, the secretion signal sequence of glucoamylase, the signal sequence of yeast α- or a-agglutinin, the secretion signal sequence of the expression product itself are suitably used for the secretion signal sequence. The secretion signal sequence and the pro-sequence may partially or entirely may remain in the N terminal without affecting the activity of a protein fused to cell surface binding proteins adversely.

Here, the GPI anchor refers to a glycolipid having a basic structure of ethanolamine-phosphate-6-mannose-α1-2-mannose-α1-6-mannose-α1-4-glucosamine-α1-6-inositol-phospholipid called glycosyl phosphatidylinositol (GPI), and PI-PLC refers to phosphatidylinositol-dependent phospholipase C.

The GPI anchor attachment recognition signal sequence is a sequence recognized upon the binding of the GPI anchor to a cell surface-localized protein and is usually located at or near the C-terminal of the cell surface-localized protein. For example, the sequence of the C-terminal portion of yeast α-agglutinin is suitably used for the GPI anchor attachment signal sequence. Since a GPI anchor attachment recognition signal sequence is contained in the C-terminal of the sequence of 320 amino acids from the C-terminal of α-agglutinin, a DNA sequence coding for the sequence of 320 amino acids from the C-terminal is particularly useful as a gene for use in the method.

Therefore, for example, in a sequence having a DNA coding for a secretion signal sequence-a structural gene coding for a cell surface-localized protein-a DNA sequence coding for a GPI anchor attachment recognition signal, the entire or a part of the sequence of the structural gene coding for a cell surface-localized protein can be replaced with a DNA sequence coding for the enzyme of interest so as to obtain a recombinant DNA for displaying the enzyme of interest on the cell surface via a GPI anchor. In case of the cell surface-localized protein is α-agglutinin, it is preferable to introduce a DNA coding for the enzyme of interest such that the sequence coding for the sequence of 320 amino acids from the C-terminal of the α-agglutinin is retained. For this purpose, the "3' half region of α-agglutinin gene" may be used. Such a recombinant DNA can be introduced into an yeast for expression to display the enzyme on the cell surface, where the enzyme is immobilized on the surface via the C-terminal.

Next, (b) use of a sugar chain binding protein domain is described. The cell surface-localized protein can be a sugar chain binding protein, and the sugar chain binding protein domain thereof has a plurality of sugar chains which can interact or be entangled with sugar chains present in the cell wall to leave the protein on the cell surface. Examples include sugar chain binding sites of lectin, lectin-like proteins, and the like. Typical examples include the flocculation functional domain of a GPI anchor protein and the flocculation functional domain of a FLO protein. The flocculation functional domain of a GPI anchor protein refers to a domain that is located on the side of N-terminal relative to the GPI anchoring domain, has a plurality of sugar chains, and is thought to be involved in flocculation.

The linkage of sugar chain binding protein domain (or flocculation functional domain) of a cell-surface localized protein with the enzyme of interest allows the enzyme to be displayed on the cell surface. Depending on the enzyme of interest, the enzyme may be linked (1) on the side of N-terminal or (2) on the side of C-terminal of the sugar chain binding protein domain (or flocculation functional domain) of a cell surface-localized protein, or the same or different enzymes may be linked (3) on both sides of N-terminal and C-terminal. In the invention, (1) a DNA coding for a secretion signal sequence-a gene coding for the enzyme of interest-a structural gene coding for the sugar chain binding protein domain (or flocculation functional domain) of a cell surface-localized protein; or (2) a DNA coding for a secretion signal sequence-a structural gene coding for the sugar chain binding protein domain (or flocculation functional domain) of a cell surface-localized protein-a gene coding for the enzyme of interest; or (3) a DNA coding for a secretion signal sequence-a gene coding for the first enzyme of interest-a structural gene coding for the sugar chain binding protein domain (or flocculation functional domain) of a cell surface-localized protein-a gene coding for the second enzyme of interest (the first and second enzymes may be same or different) may be produced to obtain a recombinant DNA for displaying the enzyme(s) of interest on the cell surface. Using the flocculation functional domain, the DNA sequence coding for a GPI anchor attachment recognition signal sequence may be partially present or may not be present in the recombinant DNA since the GPI anchor is not involved in cell surface display. The use of the flocculation functional domain is very advantageous in that: the enzyme can be displayed on the cell surface in a more suitable length because the length of the domain can be easily modified (for example, any of Floshort and Flolong can be selected); and the enzyme can be linked on either side of the N-terminal or the C-terminal.

Next, (c) use of a periplasm protein (another receptor molecule or target receptor molecule) is described. This method is based on the fact that the enzyme of interest can be expressed on the cell surface as a fused protein with the periplasm protein. An example of the periplasm protein may be invertase (Suc2 protein). The enzyme of interest may be suitably fused on the side of N-terminal or C-terminal depending on the periplasm protein.

A method for expression of an enzyme to secrete it outside an yeast cell is well known to those skilled in the art. A recombinant DNA in which the structural gene of the enzyme of interest is linked to a DNA coding for the secretion signal sequence may be prepared and introduced into an yeast.

Naturally, a method for expression of a gene in an yeast cell is also well known to those skilled in the art. In this case, a recombinant gene to which the structural gene of interest is linked without using the cell surface display factor or the secretion signal as described above may be prepared and introduced into an yeast.

The synthesis and the linkage of DNA including various sequences may be performed using techniques commonly used by those skilled in the art. For example, the linkage of the secretion signal sequence and the structural gene for the enzyme of interest can be carried out using site-directed mutagenesis technique, thereby allowing accurate cleavage of secretion signal sequence and active expression of enzyme.

An enzyme gene or an expression cassette may be inserted into a vector in a plasmid form. It is preferable that the vector is an yeast—*E. coli* shuttle vector for facilitating the procedure for obtain a DNA. The vector may contain a regulatory sequence as described above, as necessary. It is further preferable that, for example, the starting material of vector preparation has an origin of replication (Ori) of a 2 μm plasmid for yeast and an origin of replication of ColE1 as well as an yeast selectable marker (examples include drug-resistant genes and auxotrophic marker genes (for example, genes coding for imidazoleglycerol phosphate dehydrogenase (HIS3), malic acid beta-isopropylmalate dehydrogenase (LEU2), tryptophan synthase (TRP5), argininosuccinase lyase (ARG4), N-(5'-phosphoribosyl)anthranilic acid isomerase (TRP1), histidinol dehydrogenase (HIS4), orotidine-5-phosphate decarboxylase (URA3), dihydroorotic acid dehydrogenase (URA1), galactokinase (GAL1), and alpha-aminoadipic acid reductase (LYS2)) and an *E. coli* selectable marker (such as a drug resistant gene).

The "introduction" of a gene or a DNA herein means not only the introduction of a gene or a DNA into a cell but also the expression thereof. Transformation, transduction, transfection, co-transfection, electroporation, or other methods are used for gene or DNA introduction. For introduction into an yeast cell, specific examples include lithium acetate method, protoplast method, and the like. The DNA to be introduced may be present in a plasmid form or may be incorporated into a chromosome after being inserted into the gene of a host or through homologous recombination with the gene of a host.

The host yeast is a noncellulolytic yeast and this may be a wild-type yeast. The kind of yeast is not particularly limited, and in particular, yeasts that belong to the genus *Saccharomyces* are preferable, with *Saccharomyces cerevisiae* being preferable. Wild-type industrial yeasts are preferable. The wild-type yeast may be genetically modified to enhance an ability of alcoholic fermentation from a substrate monosaccharide (for example, glucose).

The term "industrial yeast" refers to any yeasts used conventionally in ethanol fermentation (for example, sake yeasts, shochu yeasts, wine yeasts, beer yeasts, baker's yeasts, and the like). Among industrial yeasts, sake yeasts are preferable in regard to high ethanol fermentability and high ethanol resistance and genetic stability. An "industrial yeast" has high ethanol resistance and preferably is viable at ethanol concentrations of 10% or greater. Moreover, it is preferable that it has acid resistance, heat resistance, and the like. More preferably, it may be flocculable. Examples of industrial yeast which has such properties include the strains *Saccharomyces cerevisiae* NBRC1440 (MATα, haploid yeast, heat resistant and acid resistant, flocculable) and NBRC1445 (MATa, haploid yeast, heat resistant and acid resistant, not flocculable) both available from the National Institute of Technology and Evaluation.

Since the industrial yeast has extremely strong ethanol resistance, it is possible to apply it directly to ethanol fermentation after monosaccharide production. In particular, the industrial yeast is preferable because it is resistant to any stresses under culturing and shows stable cell proliferation even in industrial production where a precise control of culturing conditions is difficult, which may result in severe culturing conditions. Since industrial yeasts form polyploids, it is possible to integrate a plurality of gene constructs (expression vectors) into homologous chromosomes, and as a result, the amount of the protein of interest expressed is higher compared to the integration into laboratory yeasts, which are often haploids.

Industrial yeasts are often prototrophs and lack an auxotrophic marker suitable for selecting for a transformant. Accordingly, a specific auxotrophic marker suitable for introducing a gene of interest is provided with an industrial yeast, especially, into an yeast lacking an auxotrophy and highly resistant to ethanol (preferably viable at ethanol concentrations of 10% or greater) to facilitate the introduction of the gene of interest thereinto. Examples of the auxotrophic marker include, but not limited to, uracil auxotrophy, tryptophan auxotrophy, leucine auxotrophy, histidine auxotrophy, and the like, in view of the applicability in gene manipulation. As previously described, a normal ura3 gene of industrial yeast can be replaced with an ura3⁻ fragment obtained from an uracil auxotrophic mutant (for example, *Saccharomyces cerevisiae* MT-8) to provide uracil auxotrophy. To provide an auxotrophy other than uracil auxotrophy (for example, tryptophan auxotrophy, leucine auxotrophy, histidine auxotrophy, or the like), it is possible to design a fragment so as to adopt as the target and disrupt the gene thereof, for example, according to the method described in Non-Patent Document 4.

The industrial yeast into which the gene to be expressed has been introduced by the integration of the expression cassette as mentioned above may be selected with an yeast selectable marker (for example, an auxotrophic marker mentioned above) as described above, and confirmed by determining the activity of the expressed protein. The immobilization of protein on cell surface may be confirmed by immunological antibody method using an anti-protein antibody and an FITC-labeled anti-IgG antibody.

(Ethanol Production)

The yeast having an increased cellulose hydrolysis ability as mentioned above may be suitably used in ethanol production. For ethanol production, the yeast having an increased cellulose hydrolysis ability may be reacted with a cellulosic substrate (for example, a cellulose-based material as described below).

The term "cellulose-based material" as used herein refers to any material, product, or composition which contains cellulose. The term "cellulose" refers to a fibrous polymer in which glucopyranoses are connected by a β1,4-glycosidic bond and includes derivatives and salts thereof as well as those that have a degree of polymerization reduced by decomposition.

Any material containing cellulose, including, for example, paper waste generated in production or recycling of paper, cotton products such as old clothes and waste towels, and the xylem of trees and the leaves, stems, bark, and the like (especially, non-edible portions) of herbaceous plants that are not agriculturally harvested or are disposed of in food production) is encompassed within the term "cellulose-based material." For example, cellulosic compounds such as carboxymethylcellulose (CMC), which is carboxymethylated cellulose, phosphoric acid-swollen cellulose, crystalline cellulose (for example, Avicel) and the like are encompassed within the term "cellulose-based material." Among the cellulosic compounds, phosphoric acid-swollen cellulose is suitably used as an alternative substrate of actual biomass cellulose to measure the cellololytic ability of cellulolytic enzyme.

The above illustrated cellulose-containing materials (especially, the xylem of trees and the leaves, stems and bark of herbaceous plants) may contain plant cell wall components, one of the principal components of which is cellulose. Plant cell walls usually contain, in addition to cellulose, hemicellulose and lignin as their components. Depending on the plant species (especially, whether woody or herbaceous), the extent of plant growth, or the like, the contents of such components may vary, but a plant of any species at any growth stage may be used as long as it contains cellulose.

Therefore, cellulose-based materials also include any material, waste, and product containing the plant cell wall components as mentioned above. Insoluble dietary fiber is also encompassed within the term "plant cell wall component-containing materials" Cellulose-based materials include, in addition to the xylem of trees and the leaves, stems and bark of herbaceous plants as mentioned above, products processed from such portions (for example, corn fiber), but use of discarded waste is preferable in the present invention in view of reuse.

In addition to cellulosic compounds themselves and compositions containing cellulose compounds, examples of cellulose-based materials include rice husk, bamboo, bagasse, straw, corncob, or other agricultural wastes, wooden materials (wood chip, scrap wood), old newspaper, magazine, cardboard, waste office paper, linters, cotton, pulp, and waste pulp discharged from paper manufacturers.

A cellulase enzyme may be involved in the foregoing reaction. The "cellulase enzyme" includes a cellulase enzyme of any form that is isolated as an enzyme. Examples of the "cellulase enzyme" include an enzyme isolated and purified from a microorganism that produces cellulase (i.e., endoglucanase) as described above and an enzyme produced by genetic modification using a cellulase gene. Commercially available cellulase enzymes are also usable. An example of a commercially available cellulase enzyme is Cellulase SS, Genencor, *Trichoderma reesei*-derived cellulose, a titer of 7.6 FPU/mL ("FPU" is an abbreviation for "Filter Paper Unit", with "1 FPU" being the amount of enzyme that generates 1 μmol of reducing sugars corresponding to glucose from filter paper in 1 minute). In particular, in the case where ethanol is industrially produced, a cellulase enzyme may be further added to enhance production efficiency in the reaction with a cellulose-based material.

In the reaction process as mentioned above, a hemicellulose-degradable and xylose-utilizing yeast may be further added. It may be prepared as described below. Xylose can be obtained from the enzymolysis of hemicellulose contained in cell wall components one of the principal components of which is cellulose. Xylose from hemicellulose can also be used for ethanol fermentation by separately producing an yeast (preferably, industrial yeast) that expresses a xylose utilization gene and/or a gene coding for a xylanolytic enzyme for xylose utilization. It is preferable that a hemicellulose-degrading enzyme (for example, a xylanolytic enzyme) is displayed on the cell surface of an industrial yeast. Examples of xylanolytic enzymes include xylanase (especially XYLII derived from *Trichoderma reesei*) and β-xylosidase (XylA derived from *Aspergillus oryzae*). Xylose utilization genes include genes for xylose-metabolising enzymes and examples of which include xylose reductase (XR) gene and xylitol dehydrogenase (XDH) gene (both derived from *Pichia stipitis*) and xylulokinase (XK) gene (derived from *Saccharomyces cerevisiae*).

For example, in order to prepare an industrial yeast that has both xylanolytic (hemicellulose-degrading) and xylose-utilizing properties, an industrial yeast may be recombinantly produced to express xylanase (especially XYLII derived from *Trichoderma reesei* (INSD Accession No. X69574; S51975)) and β-xylosidase (XylA derived from *Aspergillus oryzae* (INSD Accession No. AB013851)) on the cell surface and express a xylose utilization gene (especially xylose reductase (XR) gene XYL1 derived from *Pichia stipitis* (INSD Accession No. X59465), xylitol dehydrogenase (XDH) gene XYL2 derived from *Pichia stipitis* (INSD Accession No. X55392), and xylulokinase (XK) gene XKS1 derived from *Saccharomyces cerevisiae* (INSD Accession No. X82408). For the construction of expression vector and transformation, the procedures are described in Non-Patent Documents 1 and 5-7. Such genetically engineered yeasts may be referred to as hemicellulose-degradable and xylose-utilizing yeasts. The genetic engineering for preparing transformed enzymes may also be performed as described above.

The foregoing reaction process may be carried out under usual ethanol fermentation conditions. Herein, the reaction step is also referred to as a fermentation process. For example, the fermentation process may be carried out by culturing of yeast in a cellulose-based material-containing medium. The fermentation process may be carried out under usual ethanol fermentation conditions. The fermentation medium may contain further components that are necessary or desirable for the growth of yeast. Examples of the mode of the fermentation process include batch, feed-batch, repetitive batch, continuous processes, and the like, and any such process may be selected. The temperature during fermentation may be usually about 30 to 35° C. The fermentation pH may be preferably about 4 to about 6 and more preferably about 5. The fermentation culture may be carried out anaerobically (the dissolved oxygen concentration may be, for example, about 1 ppm or less, more preferably about 0.1 ppm or less, and still more preferably about 0.05 ppm or less). The load of yeast, the load of cellulose-based material, the fermentation time, and other factors may be appropriately determined according to the requirements such as the volume of fermentation reaction and the desired amount of ethanol to be produced.

Since the conditions for ethanol fermentation vary during the course of fermentation, it is preferable to control the conditions to be within a specific range. The time course of fermentation may be monitored by, for example, gas chromatography, HPLC, or a like means commonly used by those skilled in the art.

The cellulose-based material may be applied to a pressurized hot water treatment before the fermentation process. An example of a pressurized hot water treatment is a non-catalytic hydrothermal method as described in Patent Document 1. The cellulose-based material may be treated using this non-catalytic hydrothermal method such that, for example, cellulose units or oligosaccharides having a suitable length are formed or such that the crosslink between fiber chains (for example, inter-cellulose) is removed and a cellulolytic enzyme can readily act thereon. In the method described in Patent Document 1, in the case of a batch process, although depending on the concentration for treatment, starting cellulose fiber having a concentration of 10 weight % may be treated at 120 to 300° C., preferably 150 to 280° C. and more preferably 180 to 250° C., and preferably the time for treatment is generally in the range of 1 hour to 15 seconds. In the case of a continuous process, the treatment can be carried out using a slightly increased temperature owing to the time of thermal hysteresis, and starting cellulose fiber having a concentration of about 10 weight % may be treated at 120 to 373° C., and preferably 150 to 320° C., preferably for 1 hour to 1 second. In regard to pressurization, a pressure with which a temperature within the foregoing range can be achieved may be set automatically or manually depending on the apparatus.

A non-saccharified portion such as lignin may be removed in advance from the xylem of trees and the leaves, stems and barks of herbaceous plants (biomass). A pressurized hot water treatment may be employed to remove lignin. A pressurized hot water treatment can remove lignin without a reagent such as acid or alkali and is thus preferable. The method described in Patent Document 1 may be used for the pressurized hot water treatment. The method described in Patent Document 3 may also be used. In the method of Patent Document 3, biomass is treated with hot water having a temperature of 180 to 374° C. at ordinary pressures to 5 MPa and cooled to 100 to 180° C. to separate lignin.

Prior to applied to the fermentation process, a cellulose-based material may be applied to a pressurized hot water treatment, for example, according to the method described in Patent Document 1. It is thus possible that lignin (if present) is removed and cellulose is treated such that a cellulolytic enzyme can readily act thereon.

After the termination of the fermentation process, the medium, which contains ethanol, is removed from the fermenter and ethanol is isolated in the separation process commonly employed by a person skilled in the art, for example, separation with centrifugation or distillation.

An yeast having an increased cellulose hydrolysis ability (and, as necessary, a hemicellulose-degradable and xylose-utilizing yeast as well as a cellulase enzyme) is preferably immobilized on a carrier, thereby making reuse possible.

As the carrier and the method for immobilizing, carriers and methods commonly used by those skilled in the art may be used. Examples include carrier binding, entrapment, crosslinking, and the like.

A porous material is preferably used as the carrier. For example, preferable are polyvinyl alcohol, polyurethane foam, polystyrene foam, polyacrylamide, polyvinyl formal porous resin, silicone foam, and like foam and resin. The pore size of a porous material may be selected in consideration of the microorganism to be used and the size thereof. In the case of industrial yeast, the size is preferably 50 to 1000 μm.

The carrier may have any shape. In view of the strength of the carrier, culturing efficiency, and the like, the shape is preferably spherical or cubic. The size may be selected according to the microorganism to be used, and it is generally preferable that the diameter is 2 to 50 mm where the carrier is spherical and one side has a length of 2 to 50 mm where the carrier is cubic.

The yeast may be increased in number by culturing under aerobic conditions before the yeast is applied to fermentation. The medium may be a selective medium or a nonselective medium. The pH of the medium for culturing is preferably about 4 to about 6 and most preferably about 5. The concentration of dissolved oxygen in the medium for aerobic culturing is preferably about 0.5 to about 6 ppm, more preferably about 1 to about 4 ppm, and most preferably about 2 ppm. The temperature for culturing may be about 20 to about 45° C., preferably about 25 to about 35° C., and more preferably about 30° C. It is preferable to culture until the total cell concentration of yeast reaches 20 g/l (wet cells) or greater, preferably 50 g/l (wet cells) or greater, more preferably 75 g/l (wet cells) or greater, and the time for culturing may be about 20 to about 50 hours.

Conventionally, sufficient saccharification has required larger amounts of enzyme due to the lower titer of commercially available enzymes, resulting in a higher cost for enzyme for use in saccharification, which is problematic. An yeast having an increased cellulose hydrolysis ability can be used to reduce the amount of cellulase enzyme required to achieve a suitable amount or rate of ethanol production particularly for industrial production. In addition, a hemicellulose-degradable and xylose-utilizing yeast can be used in combination to enhance the ethanol production.

The present invention shall be described below by way of examples although the present invention is not limited to the examples.

EXAMPLES

The strains *Saccharomyces cerevisiae* NBRC1440 (MATα) and *Saccharomyces cerevisiae* MT8-1 (MATa ade his3 leu2 trp1 ura3) used in the examples were obtained from the National Institute of Technology and Evaluation.

All PCR amplifications presented in the examples were performed using a KOD-Plus-DNA polymerase (Toyobo Co., Ltd.).

All Yeast transformations presented in the examples were performed with lithium acetate using Yeastmaker yeast transformation system (Clontech Laboratories, Palo Alto, Calif., USA).

Preparation Example 1

Preparation of Yeasts Provided with URA3, HIS3, TRP1, and LEU2 Auxotrophic Markers Preparation Example 1-1

Provision of URA3 Marker

A mutant URA3 fragment was obtained from *Saccharomyces cerevisiae* MT8-1 (MATa ade his3 leu2 trp1 ura3) by PCR using a pair of primers having SEQ ID NOS: 1 and 2. This fragment was transformed into *Saccharomyces cerevisiae* NBRC1440 (MATα), and a URA3 variant was selected in a 5-fluoroorotic acid (FOA) medium, giving an NBRC1440 strain provided with a URA3 marker.

The 5-fluoroorotic acid (FOA) medium was prepared in the following manner. A uracil dropout synthetic dextrose (SD) medium (Non-Patent Document 8) supplemented with 50 mg/L uracil acid and 2% (w/v) agar was autoclaved and kept at 65° C. FOA was dissolved in dimethyl sulfoxide (DMSO) to a concentration of 100 mg/mL and added to the autoclaved medium having a temperature of about 65° C. to a final FOA concentration of 1 mg/mL.

Preparation Example 1-2

Provision of HIS3 Marker

Fusion PCR was carried out as follows:

In PCR1, HIS3-Green U (SEQ ID NO: 3; Forward) and HIS3-Green R (SEQ ID NO: 4; Reverse) primers were used with the chromosome DNA of *Saccharomyces cerevisiae* NBRC1440 as a template to amplify a sequence upstream of HIS3.

In PCR2, URA3 fragment (SEQ ID NO: 5; Forward) and HIS3-40Uc (SEQ ID NO: 6; Reverse) primers were used with a pRS406 plasmid (Stratagene) as a template to amplify URA3.

In PCR3, HIS3-Green U (SEQ ID NO: 3; Forward) and HIS3-40Uc (SEQ ID NO: 6; Reverse) primers were used with mixed products of PCR1 and PCR2 as a template to amplify a fused fragment.

Using the obtained fused fragment, the NBRC1440 strain provided with a URA3 marker prepared above was transformed by homologous recombination. A strain lacking a uracil auxotrophy was selected on a uracil dropout (uracil-free medium) plate. The integration of this construct into the chromosome of the foregoing industrial yeast NBRC1440, resulting in the disruption of the HIS3 gene and the integration of the URA3 marker and its flanking repeat sequences into the chromosome.

Thereafter, this transformant was grown in YPD medium at 30° C. for 24 hours. Next, the transformant was grown to $1.0 \times 10^7$ cells/200 μL on 5-FOA medium plate. All of colonies grown on 5-FOA medium plate, which have a uracil auxotrophic (Ura⁻) phenotype, were selected. The transformant grown on 5-FOA medium plate represented a uracil auxotrophic (Ura⁻) phenotype, since the URA3 marker which should have been introduced by transformation was removed from the chromosome of the transformant by the homologous recombination with the flanking repeat sequences of the URA3 marker.

Eventually, a strain lacking the HIS3 gene and the URA3 gene and having HIS3 and URA3 auxotrophies, i.e., an NBRC1440 strain provided with URA3 and HIS3 markers was obtained.

Preparation Example 1-3

Provision of TRP1 Marker

Fusion PCR was carried out as follows:

In PCR1, TRP1-988 (SEQ ID NO: 7; Forward) and RP1-28r (SEQ ID NO: 8; Reverse) primers were used with the chromosome DNA of *Saccharomyces cerevisiae* NBRC1440 as a template to amplify a sequence upstream of TRP1.

In PCR2, TRP1-URA3 (SEQ ID NO: 9; Forward) and TRP1-40r (SEQ ID NO: 10; Reverse) primers were used with a pRS406 plasmid (Stratagene) as a template to amplify URA3.

In PCR3, TRP1-988 (SEQ ID NO: 7; Forward) and TRP1-40r (SEQ ID NO: 10; Reverse) primers were used with mixed products of PCR1 and PCR2 as a template to amplify a fused fragment.

Using this fused fragment, the NBRC1440 strain provided with HIS3 and URA3 markers prepared above was transformed in the same manner as in Preparation Example 1-2, and eventually an NBRC1440 strain provided with URA3, HIS3, and TRP1 markers was obtained.

Preparation Example 1-4

Provision of LEU2 Marker

Fusion PCR was carried out as follows:

In PCR1, LEU2-UP 3rd (SEQ ID NO: 11; Forward) and LEU2-down 3rd (SEQ ID NO: 12; Reverse) primers were used with the chromosome DNA of *Saccharomyces cerevisiae* NBRC1440 as a template to amplify a sequence upstream of LEU2.

In PCR2, LEU2-URA3 3rd (SEQ ID NO: 13; Forward) and LEU2-40r (SEQ ID NO: 14; Reverse) primers were used with a pRS406 plasmid (Stratagene) as a template to amplify URA3.

In PCR3, LEU2-UP 3rd (SEQ ID NO: 11; Forward) and LEU2-40r (SEQ ID NO: 14; Reverse) primers were used with mixed products of PCR1 and PCR2 as a template to amplify a fused fragment.

Using this fused fragment, the NBRC1440 strain provided with URA3, HIS3, and TRP1 markers prepared above was transformed in the same manner as in Preparation Example 1-2, and eventually an NBRC1440 strain provided with URA3, HIS3, and TRP1, and LEU2 markers was obtained. This strain is denoted "NBRC1440/UHWL" for convenience.

Preparation Example 2

Preparation of pRS406 EG CBH2

First, a plasmid pGK406 EG, having a uracil gene (URA3) marker and for the surface-display integration of a gene for *Trichoderma reesei*-derived endoglucanase II (EGII), was constructed.

A 2719 bp DNA fragment coding for the secretion signal sequence of *Rhizopus oryzae*-derived glucoamylase gene, an EGII gene, and the 3' half of α-agglutinin gene (Non-Patent Document 9) was prepared by PCR using a pair of primers of SEQ ID NO: 15 (Forward) and SEQ ID NO: 16 (Reverse) with pEG23u31H6 (Non-Patent Document 10) as a template.

Two DNA fragments of PGK (phosphoglycerate kinase) promoter and PGK terminator were amplified by PCR using a primer pair (SEQ ID NO: 17; Forward and SEQ ID NO: 18; Reverse) and a primer pair (SEQ ID NO: 19; Forward and SEQ ID NO: 20; Reverse) designed for PGK promoter and PGK terminator, respectively, with a genomic DNA of *Saccharomyces cerevisiae* BY4741 as a template. A multicloning site was prepared by annealing a pair of primers (SEQ ID NO: 21; Forward, and SEQ ID NO: 22; Reverse) designed for the multicloning site. The PGK promoter was digested with XhoI and NheI, the multicloning site was digested with NheI and BglII, and the PGK terminator was digested with BglII and NotI, and then they were cloned into the XhoI-NotI site of pTA2 vector (Toyobo Co. Ltd., Osaka, Japan). The resultant vector was digested with XhoI and NotI, and the resultant fragment was cloned in pRS406 (Stratagene), thus giving a vector which was named pGK406.

The foregoing 2719 bp DNA fragment was digested with NheI and XmaI and inserted between the NheI site and the XmaI site of the plasmid pGK406 containing a URA3 gene and its promoter and terminator, a PGK promoter, and a PGK terminator, thus giving a plasmid containing a URA3 gene and its promoter and terminator, a PGK promoter, the secretion signal sequence of *Rhizopus oryzae*-derived glucoamylase gene, an endoglucanase (EGII) gene, the 3' half of α-agglutinin gene, and a PGK terminator. The resultant plasmid was named pGK406 EG.

A fragment containing a GAPDH (glyceraldehyde triphosphate dehydrogenase) promoter, the secretion signal sequence of *Rhizopus oryzae*-derived glucoamylase gene, a *Trichoderma reesei*-derived CBH2 gene, the 3' half of α-agglutinin gene, and a GAPDH terminator was amplified by PCR using a pair of primers (SEQ ID NO: 23; Forward, and SEQ ID NO: 24; Reverse) with a plasmid pFCBH2w3 (Non-Patent Document 11) as a template. The resultant fragment was digested with NotI and cloned in pGK406 EG digested with NotI. The resultant plasmid is referred to as pRS406 EG CBH2 and a schematic drawing thereof is shown in FIG. 1. In FIG. 1, "URA3" denotes a uracil gene marker, "GAPDH" denotes a glyceraldehyde-3-phosphate dehydrogenase promoter, "PGK" denotes a phosphoglycerate kinase promoter, "s.s." denotes the secretion signal sequence of *Rhizopus oryzae*-derived glucoamylase gene, "AG" denotes the 3' half of α-agglutinin gene, "EG" denotes a *Trichoderma reesei*-derived EGII gene, "CBH2" denotes a *Trichoderma reesei*-derived cellobiohydrolase 2 gene, "tGAP" denotes a glyceraldehyde-3-phosphate dehydrogenase terminator, and "tPGK" denotes a phosphoglycerate kinase terminator.

Preparation Example 3

Preparation of pRS403 EG CBH2

First, a plasmid pGK403 EG, having a histidine gene (HIS3) marker and for the surface-display integration of a gene for *Trichoderma reesei*-derived endoglucanase II (EGII), was constructed.

A fragment containing a PGK promoter, the secretion signal sequence of *Rhizopus oryzae*-derived glucoamylase gene, an EGII gene, and a PGK terminator was cut out from pGK406 using ApaI and NotI, and cloned in pRS403 (Stratagene) similarly digested with ApaI and NotI. The resultant plasmid was named pGK403 EG.

Figure 2:
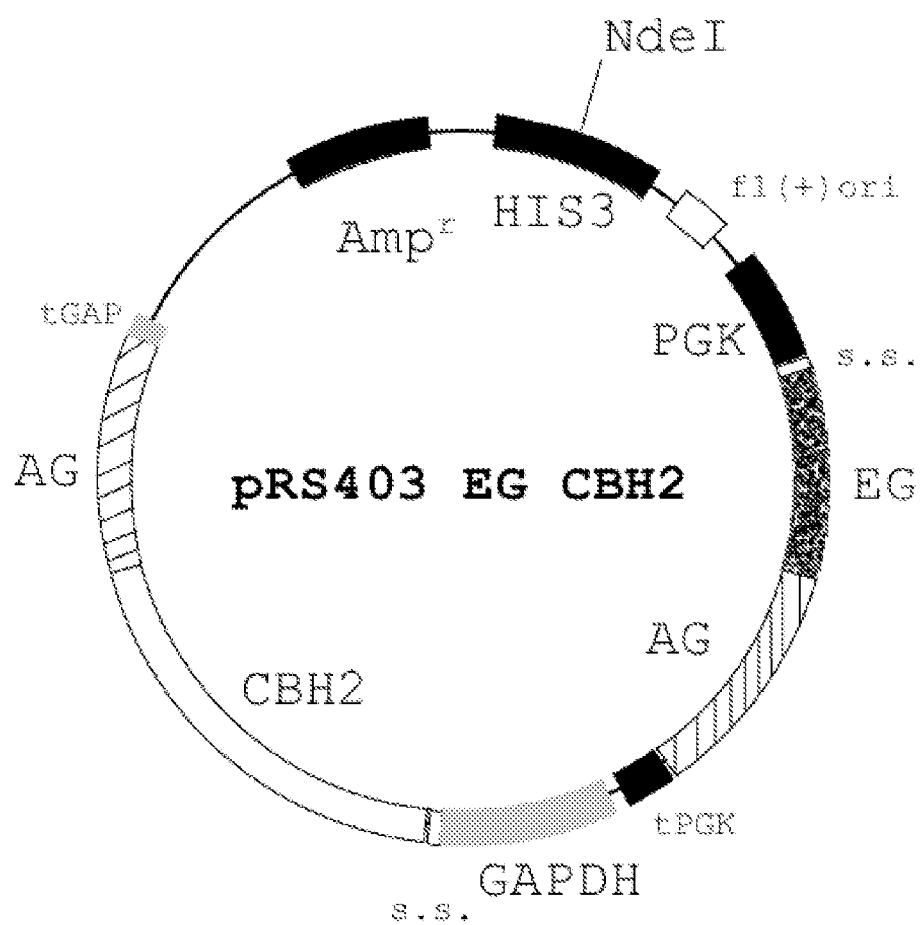
FIG. 2 is a schematic drawing of a plasmid pRS403 EG CBH2.

A fragment containing a GAPDH (glyceraldehyde triphosphate dehydrogenase) promoter, the secretion signal sequence of *Rhizopus oryzae*-derived glucoamylase gene, a *Trichoderma reesei*-derived CBH2 gene, the 3' half of α-agglutinin gene, and a GAPDH terminator was amplified by PCR using primers (SEQ ID NO: 23; Forward, and SEQ ID NO: 24; Reverse) with a plasmid pFCBH2w3 as a template. The resultant fragment was digested with NotI and cloned in pGK403 EG digested with NotI. The resultant plasmid was named pRS403 EG CBH2 and a schematic drawing thereof is shown in FIG. 2. In FIG. 2, "HIS3" denotes a histidine gene marker and the other notations are the same as in FIG. 1.

Preparation Example 4

Preparation of pRS405 EG CBH2

First, a plasmid pGK405 EG, having a leucine gene (LEU2) marker and for the surface-display integration of a gene for *Trichoderma reesei*-derived endoglucanase II (EGII), was constructed.

A fragment containing a PGK promoter, a *Rhizopus oryzae*-derived glucoamylase gene secretion signal sequence, an EGII gene, and a PGK terminator was cut out from pGK406 using ApaI and NotI, and similarly pRS405 (Stratagene) was digested with ApaI and NotI for cloning. The obtained plasmid was named pGK405 EG.

Figure 3:
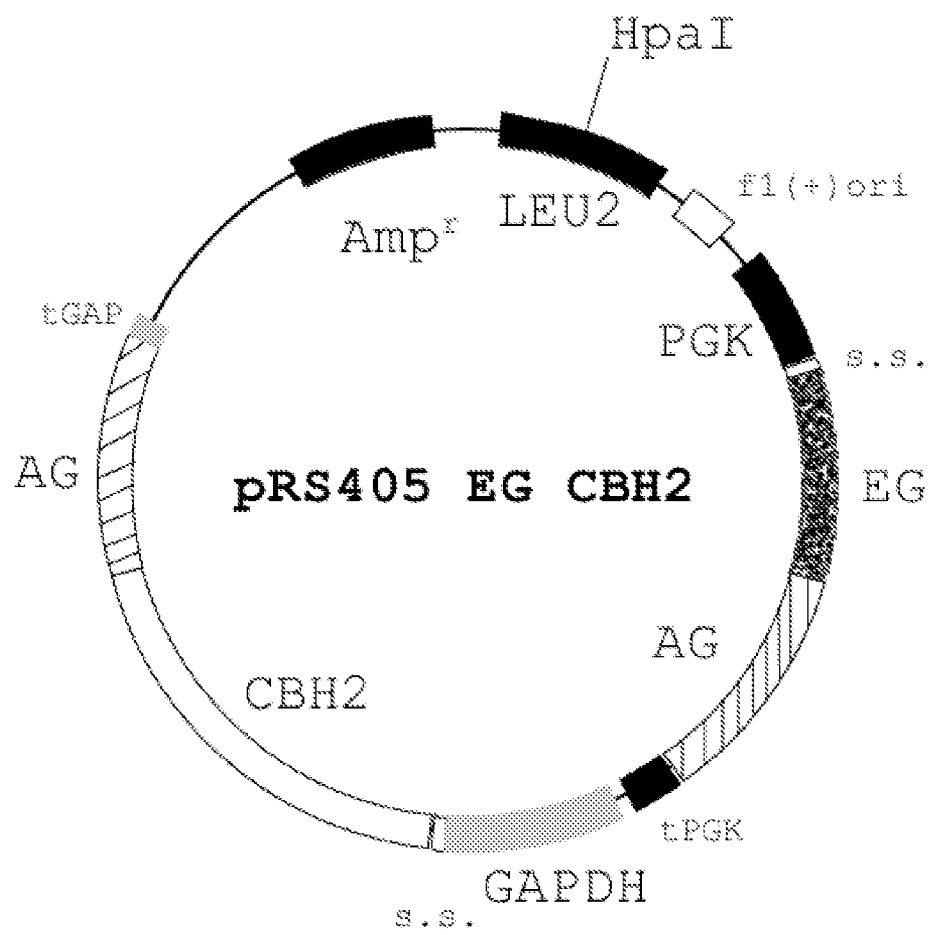
FIG. 3 is a schematic drawing of a plasmid pRS405 EG CBH2.

A fragment containing a GAPDH (glyceraldehyde triphosphate dehydrogenase) promoter, the secretion signal sequence of *Rhizopus oryzae*-derived glucoamylase gene, a *Trichoderma reesei*-derived CBH2 gene, the 3' half of α-agglutinin gene, and a GAPDH terminator was amplified by PCR using primers (SEQ ID NO: 23; Forward and SEQ ID NO: 24; Reverse) with a plasmid pFCBH2w3 as a template. The resultant fragment was digested with NotI and cloned in pGK405 EG digested with NotI. The resultant plasmid was named pRS405 EG CBH2 and a schematic drawing thereof is shown in FIG. 3. In FIG. 3, "LEU2" denotes a leucine gene marker and the other notations are the same as in FIG. 1.

Preparation Example 5

Preparation of pILGP3-CBH2

A gene sequence coding for a GAPDH promoter, a multicloning site (SalI, XbaI, BamHI, SmaI, XmaI), and a GAPDH terminator was amplified by PCR using a pair of primers XYL2c-XhoI (F) (SEQ ID NO: 25; Forward) and XYL2c-NotI (R) (SEQ ID NO: 26; Reverse) with pUGP3 (Non-Patent Document 12) as a template. This fragment was introduced into the XhoI/NotI site of pRS405 (Stratagene), giving a plasmid pILGP3.

Figure 4:
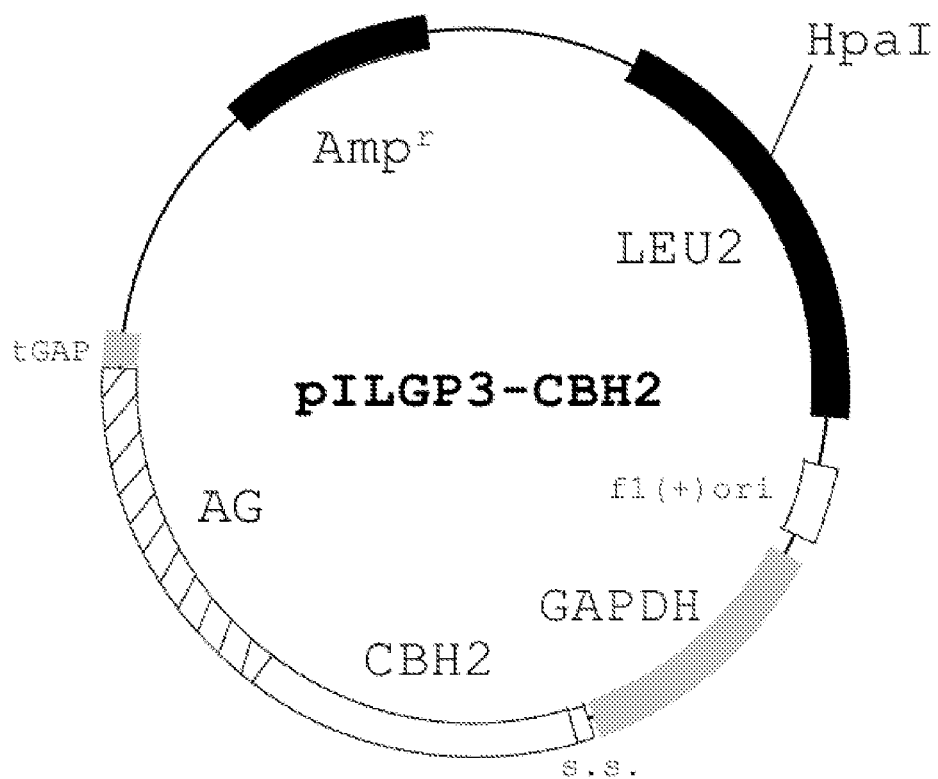
FIG. 4 is a schematic drawing of a plasmid pILGP3-CBH2.

A 2816 bp DNA fragment derived from a plasmid pFCBH2w3 prepared as described in Preparation Examples 2 to 4 above was digested with XmaI and XbaI and inserted between the XmaI site and the XbaI site of the plasmid pILGP3 containing a GAPDH promoter and a GAPDH terminator, thus giving a plasmid containing a LEU2 gene and its promoter and terminator, a GAPDH promoter, the secretion signal sequence of *Rhizopus oryzae*-derived glucoamylase gene, a *Trichoderma reesei*-derived cellobiohydrolase (CBH2) gene, the 3' half of α-agglutinin gene, and a GAPDH terminator. The resultant plasmid was named pILGP3-CBH2 and a schematic drawing thereof is shown in FIG. 4. In FIG.

4, "LEU2" denotes a leucine gene marker and the other notations are the same as in FIG. 1.

Preparation Example 6

Preparation of pRS405 CBH2 CBH2

Figure 5:
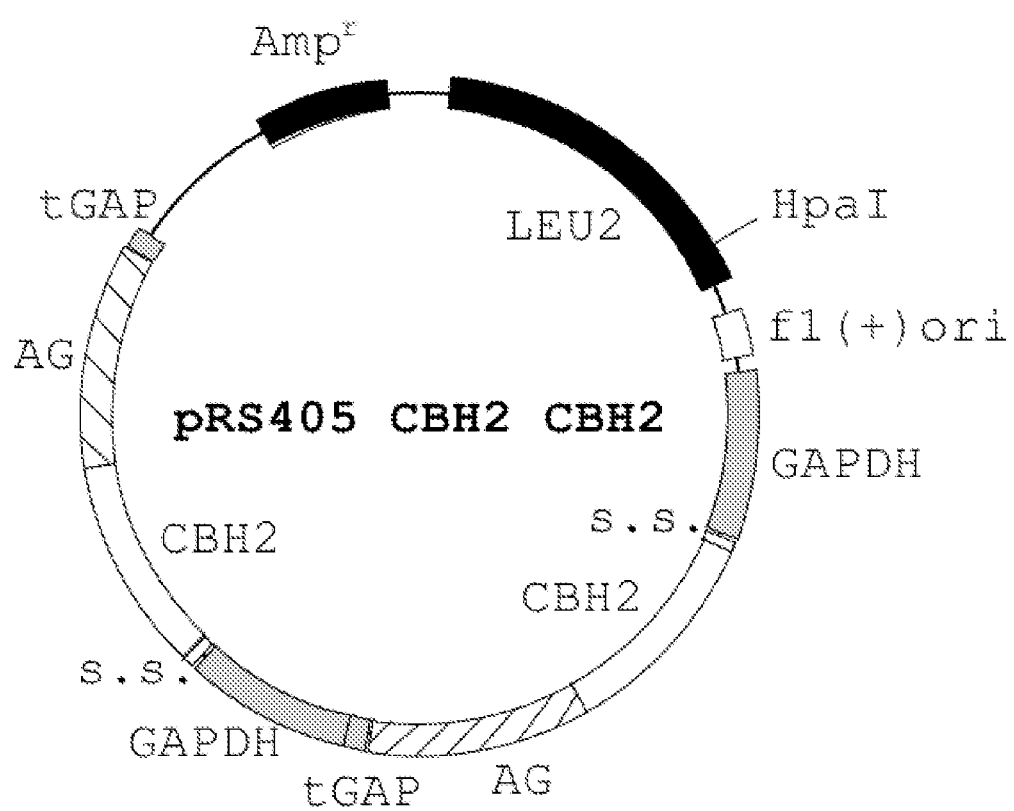
FIG. 5 is a schematic drawing of a plasmid pRS405 CBH2 CBH2.

A fragment containing a GAPDH (glyceraldehyde triphosphate dehydrogenase) promoter, the secretion signal sequence of *Rhizopus oryzae*-derived glucoamylase gene, a *Trichoderma reesei*-derived CBH2 gene, the 3' half of α-agglutinin gene, and a GAPDH terminator was amplified by PCR using primers (SEQ ID NO: 23; Forward, and SEQ ID NO: 24; Reverse) with a plasmid pFCBH2w3 as a template. The resultant fragment was digested with NotI and cloned in pILGP3-CBH2 digested with NotI. The resultant plasmid was named pRS405 CBH2 CBH2 and a schematic drawing thereof is shown in FIG. 5. In FIG. 5, "LEU2" denotes a leucine gene marker and the other notations are the same as in FIG. 1.

Preparation Example 7

Preparation of pIWBGL

A 2.5 kbp NcoI-XhoI DNA fragment coding for an *Aspergillus aculeatus*-derived β-glucosidase 1 (BGL1) gene was prepared by PCR using a pair of bgl1 primer 1 (SEQ ID NO: 27; Forward) and bgl1 primer 2 (SEQ ID NO: 28; Reverse) with a plasmid pBG211 (donated by Kyoto University) as a template. This DNA fragment was digested with NcoI and XhoI and inserted into the NcoI-XhoI site of a cell surface expression plasmid pIHCS (Non-Patent Document 10) containing the secretion signal sequence of *Rhizopus oryzae*-derived glucoamylase gene and the 3' half of α-agglutinin gene (Non-Patent Document 9). The resultant plasmid was named pIBG13.

Figure 6:
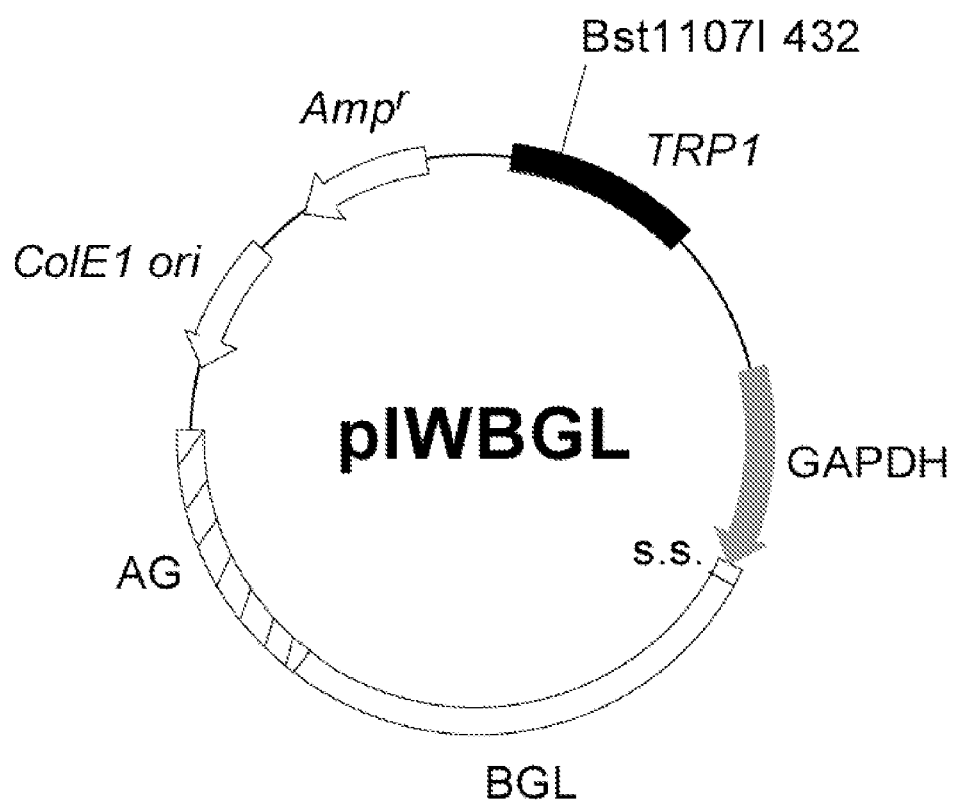
FIG. 6 is a schematic drawing of a plasmid pIWBGL.

With this pIBG13 as a template, PCR was carried out using a pair of primers (SEQ ID NO: 23; Forward and SEQ ID NO: 24; Reverse), giving a fragment containing a GAPDH promoter, the secretion signal sequence of *Rhizopus oryzae*-derived glucoamylase, a BGL1 gene, the 3' half of α-agglutinin gene, and a GAPDH terminator. This fragment was digested with NotI and cloned in pRS404 digested with NotI. The resultant plasmid was named pIWBGL and a schematic drawing thereof is shown in FIG. 6. In FIG. 6, "TRP1" denotes a tryptophan gene marker, "GAPDH" denotes a glyceraldehyde-3-phosphate dehydrogenase promoter, "s.s." denotes the secretion signal sequence of *Rhizopus oryzae*-derived glucoamylase gene, "AG" denotes the 3' half of α-agglutinin gene, and "BGL" denotes an *Aspergillus aculeatus*-derived β-glucosidase 1 (BGL1) gene.

Preparation Example 8

Preparation of Yeast Strain Having Endoglucanase II Integrated in a Copy Number of 1

NBRC1440/UHWL was transformed with pGK406 EG processed into a linear form by cleaving it with a restriction enzyme NdeI, and a strain lacking uracil auxotrophy was selected on uracil dropout (uracil-free medium) plate. Gene introduction was confirmed by the restoration of the destroyed URA3 gene in NBRC1440/UHWL on the transformation with pGK406 EG. The resultant strain was named "NBRC1440/pGK406 EG." In Preparation Example 8, a strain having endoglucanase II in a copy number of 1 to be surface-displayed was created.

Preparation Example 9

Preparation of Yeast Strain Having Endoglucanase II and Cellobiohydrolase 2 Integrated Both in a Copy Number of 1

NBRC1440/UHWL was transformed with pRS406 EG CBH2 processed into a linear form by cleaving it with a restriction enzyme NdeI, and a strain lacking uracil auxotrophy was selected on uracil-dropout (uracil-free medium) plate. Gene introduction was confirmed by the restoration of the destroyed URA3 gene in NBRC1440/UHWL on the transformation with pRS406 EG CBH2. The resultant strain was named "NBRC1440/pRS406 EG CBH2" which may also be simply referred to as "NBRC1440/EG-CBH2-1c". In Preparation Example 9, a strain having endoglucanase II and cellobiohydrolase 2 both in a copy number of 1 to be surface-displayed was created.

Preparation Example 10

Preparation of Yeast Strain Having Endoglucanase II and Cellobiohydrolase 2 Integrated Both in a Copy Number of 2

NBRC1440/pRS406 EG CBH2 was transformed with pRS403 EG CBH2 processed into a linear form by cleaving it with a restriction enzyme NdeI, and a strain lacking histidine auxotrophy was selected on histidine dropout (histidine-free medium) plate. Gene introduction was confirmed by the restoration of the destroyed HIS3 gene in NBRC1440/pRS406 EG CBH2 on the transformation with pRS403 EG CBH2. The resultant strain was named "NBRC1440/pRS406 EG CBH2/pRS403 EG CBH2" which may also be simply referred to as "NBRC1440/EG-CBH2-2c". In Preparation Example 10, a strain having endoglucanase II and cellobiohydrolase 2 both in a copy number of 2 to be surface-displayed was created.

Preparation Example 11

Preparation of Yeast Strain Having Endoglucanase II and Cellobiohydrolase 2 Integrated Both in a Copy Number of 3

NBRC1440/pRS406 EG CBH2/pRS403 EG CBH2 was transformed having pRS405 EG CBH2 processed into a linear form by cleaving it with a restriction enzyme HpaI, and a strain lacking leucine auxotrophy was selected on leucine dropout (leucine-free medium) plate. Gene introduction was confirmed by the restoration of the destroyed LEU2 gene in NBRC1440/pRS406 EG CBH2/pRS403 EG CBH2 on the transformation with pRS405 EG CBH2. The resultant strain was named "NBRC1440/pRS406 EG CBH2/pRS403 EG CBH2/pRS405 EG CBH2" which may also be simply referred to as "NBRC1440/EG-CBH2-3c". In Preparation Example 11, a strain having endoglucanase II and cellobiohydrolase 2 both in a copy number of 3 to be surface-displayed was created.

Preparation Example 12

Preparation of Yeast Strain Having Endoglucanase II and Cellobiohydrolase 2 Integrated Both in a Copy Number of 1 and Further Cellobiohydrolase 2 Integrated in a Copy Number of 1

NBRC1440/pRS406 EG CBH2 was transformed with pILGP3-CBH2 processed into a linear form by cleaving it with a restriction enzyme HpaI, and a strain lacking leucine auxotrophy was selected on leucine dropout (leucine-free medium) plate. Gene introduction was confirmed by the restoration of the destroyed LEU2 gene in NBRC1440/pRS406 EG CBH2 on the transformation with pILGP3-CBH2. The resultant strain was named "NBRC1440/pRS406 EG CBH2/pILGP3-CBH2" which strain may also be simply referred to as "NBRC1440/EG-CBH2-1c-CBH2". In Preparation Example 12, a strain having endoglucanase II in a copy number of 1 and cellobiohydrolase 2 in a copy number of 2 to be surface-displayed was created.

Preparation Example 13

Preparation of Yeast Strain Having Endoglucanase II and Cellobiohydrolase 2 Integrated Both in a Copy Number of 1 and Further Cellobiohydrolase 2 Integrated in a Copy Number of 2

NBRC1440/pRS406 EG CBH2 was transformed with pRS405 CBH2 CBH2 processed into a linear form by cleaving it with a restriction enzyme HpaI, and a strain lacking leucine auxotrophy was selected on leucine dropout (leucine-free medium) plate. Gene introduction was confirmed by the restoration of the destroyed LEU2 gene of NBRC1440/pRS406 EG CBH2 on the transformation with pRS405 CBH2 CBH2. The resultant strain was named "NBRC1440/pRS406 EG CBH2/pRS405 CBH2 CBH2" which may also be simply referred to as "NBRC1440/EG-CBH2-1c-CBH2×2". In Preparation Example 13, a strain having endoglucanase II in a copy number of 1 and cellobiohydrolase 2 in a copy number of 3 to be surface-displayed was created.

Preparation Example 14

Integration of Gene for β-Glucosidase 1 for Surface Display

NBRC1440/EG-CBH2-1c (Preparation Example 9), NBRC1440/EG-CBH2-2c (Preparation Example 10), and NBRC1440/EG-CBH2-3c (Preparation Example 11) were transformed with pIWBGL processed into a linear form by cleaving it with Bst1107I. A strain lacking tryptophan auxotrophy was selected on tryptophan dropout (tryptophan-free medium) plate. Introduction of the β-glucosidase 1 gene was confirmed by the restoration of the destroyed TRP1 gene in each strain on the transformation with pIWBGL. Thus, strains having endoglucanase II and cellobiohydrolase both in a copy number of 1, 2, or 3 to be surface-displayed and also β-glucosidase 1 to be surface-displayed were obtained. The resultant transformants were simply denoted "NBRC1440/EG-CBH2-1c/BGL", "NBRC1440/EG-CBH2-2c/BGL", and "NBRC1440/EG-CBH2-3c/BGL", respectively (for convenience, which may also be referred to as "cellulase surface-displaying yeasts").

Example 1

Evaluation of Cellulose Hydrolysis Ability

The various yeasts obtained in the foregoing Preparation Examples 8 to 13 were reacted with phosphoric acid swollen cellulose (PSC; prepared according to Non-Patent Document 13) to measure the cellulose hydrolysis ability of the yeasts. The reaction conditions were as follows: 50 mM citrate buffer, 10 mg/mL PSC, yeast $OD_{600=3.0}$, reaction time of 24 hours. For activity measurement, the reducing sugars generated by PSC degradation were quantified according to the Somogyi-Nelson method. 1 U corresponds to the amount of yeast that generates 1 μmol of reducing sugars corresponding to glucose in 1 minute.

Figure 7:
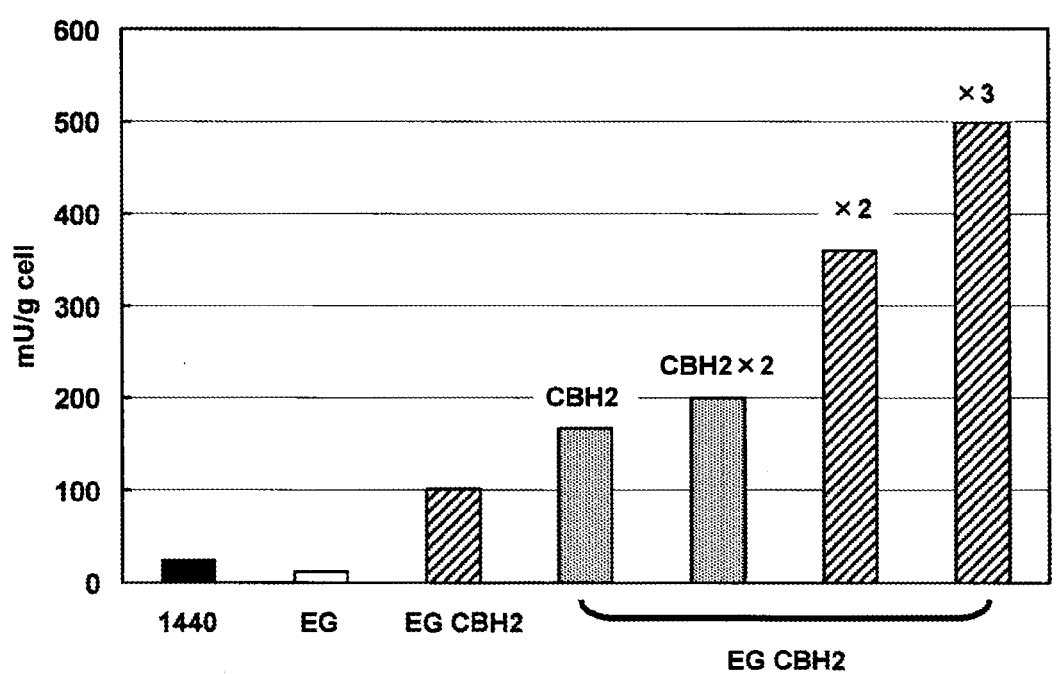
FIG. 7 is a graph showing the cellulose hydrolysis abilities of yeasts for various expressions of endoglucanase and cellobiohydrolase.

FIG. 7 is a graph showing the cellulose hydrolysis abilities of yeasts for various expressions of endoglucanase and cellobiohydrolase. In the graph, the vertical axis indicates the enzyme activity per 1 g of yeast cell (mU/g cell). In the graph, the results of the following yeast strains are presented from left to right along the horizontal axis:

NBRC1440 ("1440" in the graph),
NBRC1440/pGK406 EG ("EG" in the graph; Preparation Example 8: yeast strain having endoglucanase II integrated in a copy number of 1),
NBRC1440/EG-CBH2-1c ("EG CBH2" in the graph; Preparation Example 9: yeast strain having endoglucanase II and cellobiohydrolase 2 integrated both in a copy number of 1,
NBRC1440/EG-CBH2-1c-CBH2 ("CBH2" of "EG CBH2" in the graph; Preparation Example 12: yeast strain having endoglucanase II and cellobiohydrolase 2 integrated both in a copy number of 1 and further cellobiohydrolase 2 integrated in a copy number of 1),
NBRC1440/EG-CBH2-1c-CBH2×2 ("CBH2×2" of "EG CBH2" in the graph; Preparation Example 13: yeast strain having endoglucanase II and cellobiohydrolase 2 integrated both in a copy number of 1 and further cellobiohydrolase 2 integrated in a copy number of 2),
NBRC1440/EG-CBH2-2c ("×2" of "EG CBH2" in the graph; Preparation Example 10: yeast strain having endoglucanase II and cellobiohydrolase 2 integrated both in a copy number of 2), and
NBRC1440/EG-CBH2-3c ("×3" of "EG CBH2" in the graph; Preparation Example 11: yeast strain having endoglucanase II and cellobiohydrolase 2 integrated both in a copy number of 3).

In order to strengthen the cellulose hydrolysis ability, an attempt was made to increase the copy number of CBH (this acts on crystalline cellulose) so as to enhance the hydrolysis of the crystalline portion that was thought to be most difficult to undergo hydrolysis. However, it was found that the ability to degrade PSC is far more improved by increasing the copy number of EG together with increasing the copy number of CBH, than increasing the copy number of CBH alone.

Example 2

Examination for Ethanol Fermentation

In Example 1, the PSC degrading activity was enhanced as the copy number of the "EG CBH2" combination was increased. Therefore, in this example, strains into which a vector containing two-cassette "EG CBH2" (cassettes of 2 genes for EG and CBH2) had been integrated in one, two, and three copies, respectively, were used in ethanol fermentation from PSC.

In this example, strains prepared by integrating pIWBGL (surface display expression vector for β-glucosidase) into those three strains (NBRC1440/EG-CBH2-1c, NBRC1440/EG-CBH2-2c, NBRC1440/EG-CBH2-3c) as described in Preparation Example 14 were used. That is, three types of cellulase surface-displaying yeasts, i.e., "NBRC1440/EG-CBH2-1c/BGL", "NBRC1440/EG-CBH2-2c/BGL", and "NBRC1440/EG-CBH2-3c/BGL" were used.

The yeasts were pre-cultured aerobically (dissolved oxygen level of about 2 ppm) for 24 hours at a pH of about 5.0 at about 30° C. in SD medium (synthetic dextrose medium:

containing 6.7 g/L of yeast nitrogen base without amino acids (manufactured by Difco) and appropriate supplements; 20 g/L of glucose added as a sole carbon source) supplemented with essential amino acids, and then cultured in YPD medium (yeast extract-polypeptone-dextrose medium: containing 10 g/L of yeast extract, 20 g/L of polypeptone, and 20 g/L of glucose) under the same conditions. The culture supernatant and cell pellets were separated by centrifugation at 6000×g at 4° C. for 10 minutes to collect the cell pellets.

The cell pellets were inoculated into a fermentation medium containing 11.2 g/L of PSC, 10 g/L of yeast extract, 20 g/L of polypeptone, 50 mM of citrate buffer (pH 5.0), and 0.5 g/L of potassium metabisulfite. The subsequent fermentation was performed anaerobically (dissolved oxygen level of about 0.05 ppm) at 30° C. At the beginning of fermentation, the cell concentration was adjusted to 75 g/L (wet cells). Since the amount of PSC added was 11.2 g/L, the theoretical yield of ethanol was 5.7

The ethanol concentration during fermentation was measured using HPLC. The HPLC analysis was performed using a refractive index (RI) detector (L-2490 RI detector, Hitachi, Ltd.). The column used for separation was Shim-pack SPR-Pb Column (Shimadzu Corporation). HPLC was carried out at 80° C. with water at a flow rate of 0.6 mL/min as a mobile phase.

Figure 8:
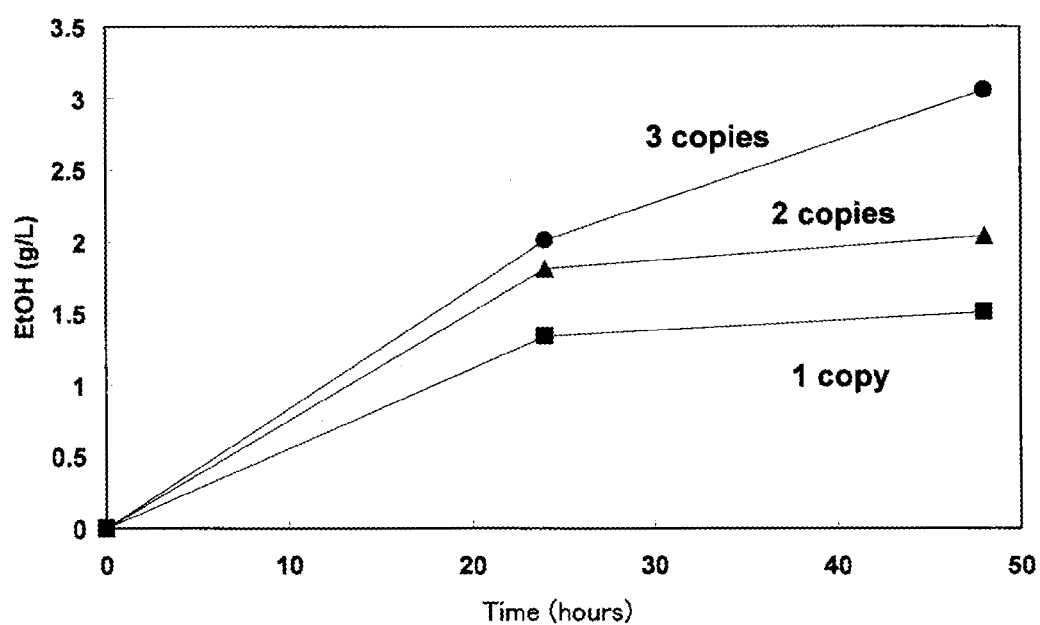
FIG. 8 is a graph showing the time course in amount of the ethanol production in fermentation from phosphoric acid swollen cellulose (PSC) by three types of cellulase surface-displaying yeasts having linearly increased copy numbers of endoglucanase and cellobiohydrolase.

FIG. 8 shows the results. FIG. 8 is a graph showing the time course in amount of the ethanol production in fermentation from PSC by three types of cellulase surface-displaying yeasts having linearly increased copy numbers of endoglucanase and cellobiohydrolase, i.e., NBRC1440/EG-CBH2-1c/BGL, NBRC1440/EG-CBH2-2c/BGL, and NBRC1440/EG-CBH2-3c/BGL. In FIG. 8, the left vertical axis indicates ethanol concentration (g/L) and the horizontal axis indicates elapsed time (hours). The results of ethanol production by the integrated yeasts NBRC1440/EG-CBH2-3c/BGL (endoglucanase II and cellobiohydrolase 2 both in three copies); NBRC1440/EG-CBH2-2c/BGL (endoglucanase II and cellobiohydrolase 2 both in two copies); and NBRC1440/EG-CBH2-1c/BGL (endoglucanase II and cellobiohydrolase 2 both in one copy) are represented by black circle, black triangle and black square, respectively.

It was demonstrated that the yield of ethanol fermentation from PSC is increased with the increased copy numbers of endoglucanase and cellobiohydrolase relative to one copy of β-glucosidase. The yield by NBRC1440/EG-CBH2-3c/BGL (which is an yeast having three copies of endoglucanase and cellobiohydrolase integrated relative to one copy of β-glucosidase) at 48 h was 52.6% of the theoretical yield.

Preparation Example 15

Cellulase Secreting Yeast

Hereinbelow, procedures of preparing an yeast on which integration was performed such that endoglucanase and cellobiohydrolase were secreted while β-glucosidase was surface-displayed (for convenience, this may also be referred to as a "cellulase secreting yeast") will be described.

Preparation Example 15-1 pRS403/ssEG2-CBH2 Plasmid

A plasmid pRS403/ssEG2-CBH2, having a histidine gene (HIS3) marker and for the secretory integration of endoglucanase II (EGII) and cellobiohydrolase 2 (CBH2), was constructed.

A gene sequence coding for a GAPDH promoter, a multi-cloning site (SalI, XbaI, BamHI, SmaI, XmaI), and a GAPDH terminator was amplified by PCR using a pair of primers XYL2c-XhoI(F) (SEQ ID NO:25; Forward) and XYL2c-NotI (R) (SEQ ID NO: 26; Reverse) with pUGP3 (Non-Patent Document 12) as a template. This fragment was introduced into the XhoI/NotI site of pRS403 (Stratagene), giving a plasmid pIHGP3.

A 1308 bp DNA fragment containing the secretion signal sequence of Rhizopus oryzae-derived glucoamylase gene and a Trichoderma reesei-derived encoglucanase (EGII) gene was prepared by PCR using a pair of primers of SEQ ID NO: 29 (Forward) and SEQ ID NO: 30 (Reverse) with pEG23u31H6 (Non-Patent Document 10) as a template.

The 1308 bp DNA fragment was digested with SmaI and inserted into the SmaI portion of the plasmid pIHGP3 containing a HIS3 gene and its promoter and terminator, a GAPDH promoter, and a GAPDH terminator, thus giving a plasmid containing a HIS3 gene and its promoter and terminator, a GAPDH promoter, the secretion signal sequence of glucoamylase gene, an EGII gene, and a GAPDH terminator. The resultant plasmid was named pRS403/ssEG2.

A 1416 bp DNA fragment containing the secretion signal sequence of Rhizopus oryzae-derived glucoamylase gene, and a Trichoderma reesei-derived CBH2 gene was prepared by PCR using a pair of primers of SEQ ID NO: 31 (Forward) and SEQ ID NO: 32 (Reverse) with a plasmid pFCBH2w3 (Non-Patent Document 11) as a template.

The 1416 bp DNA fragment was digested with SmaI and inserted into the SmaI portion of the plasmid pIHGP3 containing a HIS3 gene and its promoter and terminator, a GAPDH promoter, and a GAPDH terminator, thus giving a plasmid containing a HIS3 gene and its promoter and terminator, a GAPDH promoter, the secretion signal sequence of glucoamylase gene, an CBH2 gene, and a GAPDH terminator. The resultant plasmid was named pRS403/ssCBH2.

A fragment containing a GAPDH (glyceraldehyde triphosphate dehydrogenase) promoter, the secretion signal sequence of Rhizopus oryzae-derived glucoamylase gene, a Trichoderma reesei-derived CBH2 gene, and a GAPDH terminator was amplified by PCR using primers (SEQ ID NO: 23; Forward and SEQ ID NO: 24; Reverse) with a plasmid pFCBH2w3 as a template. The resultant fragment was digested with NotI and cloned in pRS403/ssEG2 digested with NotI. The resultant plasmid was named pRS403/ssEG2-CBH2.

Preparation Example 15-2 pRS405/ssEG2-CBH2 Plasmid

A fragment containing a GAPDH promoter, a Rhizopus oryzae-derived glucoamylase gene secretion signal sequence, a cellobiohydrolase 2 (CBH2) gene, and a GAPDH terminator was obtained by digesting pRS403/ssCBH2 with ApaI and NotI.

pRS405 having an LEU2 gene marker (Stratagene) was digested with ApaI and NotI, into which the fragment obtained above was inserted. The resultant plasmid was named pRS405/ssCBH2.

PCR amplification was performed using primers (SEQ ID NO: 23; Forward and SEQ ID NO: 24; Reverse) with a plasmid pRS403/ssEG2 as a template. The resultant fragment was digested with NotI and cloned in pRS405/ssCBH2 digested with NotI. The resultant plasmid was named pRS405/ssEG2-CBH2.

Preparation Example 15-3 pRS406/ssEG2-CBH2 Plasmid

A fragment containing a GAPDH promoter, the secretion signal sequence of *Rhizopus oryzae*-derived glucoamylase gene, a cellobiohydrolase 2 (CBH2) gene, and a GAPDH terminator was obtained by digesting pRS403/ssCBH2 with ApaI and NotI.

pRS406 having a URA3 gene marker (Stratagene) was digested with ApaI and NotI, into which the fragment obtained above was inserted. The resultant plasmid was named pRS406/ssCBH2.

PCR amplification was performed using primers (SEQ ID NO: 23; Forward and SEQ ID NO: 24; Reverse) with a plasmid pRS403/ssEG2 as a template. The resultant fragment was digested with NotI and cloned in pRS406/ssCBH2 digested with NotI. The resultant plasmid was named pRS406/ssEG2-CBH2.

Preparation Example 15-4

Preparation of Yeast Strain Having Secretory Endoglucanase II and Cellobiohydrolase 2 Integrated Both in a Copy Number of 1

NBRC1440/UHWL was transformed with pRS406/ssEG2-CBH2 processed into a linear form by cleaving it with a restriction enzyme NdeI, and a strain lacking uracil auxotrophy was selected on uracil dropout (uracil-free medium) plate. Gene introduction was confirmed by the restoration of the destroyed URA3 gene in NBRC1440/UHWL on the transformation with pRS406/ssEG2-CBH2. The resultant strain was named "NBRC1440/pRS406/ssEG2-CBH2" which may also be simply referred to as "NBRC1440/ss-EG-CBH2-1c". In this preparation example, a strain having endoglucanase II and cellobiohydrolase 2 both in a copy number of 1 to be secreted was created.

Preparation Example 15-5

Preparation of Yeast Strain into which Endoglucanase II and Cellobiohydrolase 2 Integrated Both in a Copy Number of 2

NBRC1440/pRS406/ssEG2-CBH2 was transformed with pRS403/ssEG2-CBH2 processed into a linear form by cleaving it with a restriction enzyme NdeI, and a strain lacking histidine auxotrophy was selected on histidine dropout (histidine-free medium) plate. Gene introduction was confirmed by the restoration of the destroyed HIS3 gene in NBRC1440/pRS406/ssEG2-CBH2 on the transformation with pRS403/ssEG2-CBH2. The resultant strain was named "NBRC1440/pRS406/ssEG2-CBH2/pRS403/ssEG2-CBH2" which may also be simply referred to as "NBRC1440/ss-EG-CBH2-2c". In this preparation example, a strain having endoglucanase II and cellobiohydrolase 2 both in a copy number of 2 to be secreted was created.

Preparation Example 15-6

Preparation of Yeast Strain Having Endoglucanase II and Cellobiohydrolase 2 Integrated Both in a Copy Number of 3

NBRC1440/pRS406/ssEG2-CBH2/pRS403/ssEG2-CBH2 was transformed with pRS405 ssEG2-CBH2 processed into a linear form by cleaving it with a restriction enzyme HpaI, and a strain lacking leucine auxotrophy was selected on leucine dropout (leucine-free medium) plate. Gene introduction was confirmed by the restoration of the destroyed LEU2 gene in NBRC1440/pRS406/ssEG2-CBH2/pRS403/ssEG2-CBH2 on the transformation with pRS405 ssEG2-CBH2. The resultant strain was named "NBRC1440/pRS406/ssEG2-CBH2/pRS403/ssEG2-CBH2/pRS405 ssEG2-CBH2" which may also be simply referred to as "NBRC1440/ss-EG-CBH2-3c". In this preparation example, a strain having endoglucanase II and cellobiohydrolase 2 both in a copy number of 3 to be secreted was created.

Preparation Example 15-7

Integration of β-glucosidase 1 Gene

NBRC1440/ss-EG-CBH2-1c, NBRC1440/ss-EG-CBH2-2c, and NBRC1440/ss-EG-CBH2-3c were transformed with pIWBGL processed into a linear form by cleaving it with Bst1107I. A strain lacking tryptophan auxotrophy was selected on tryptophan dropout (tryptophan-free medium) plate. Introduction of the β-glucosidase 1 gene was confirmed by the restoration of the destroyed TRP1 gene in each strain on the transformation with pIWBGL. These strains are also simply denoted "NBRC1440/ss-EG-CBH2-1c/BGL", "NBRC1440/ss-EG-CBH2-2c/BGL", and "NBRC1440/ss-EG-CBH2-3c/BGL", respectively. In this preparation example, secreting strains of Preparation Examples 15-4 to 15-6 with one copy of β-glucosidase to be surface-displayed were created.

Example 3

Comparison of Cellulase Surface-Displaying Yeast with Cellulase Secreting Yeast for Ethanol Production from Phosphoric Acid Swollen Cellulose Cell pellets of any of NBRC1440/EG-CBH2-1c/BGL, NBRC1440/EG-CBH2-2c/BGL and NBRC1440/EG-CBH2-3c/BGL, which were cellulase surface-displaying yeasts (Preparation Example 14) as well as NBRC1440/ss-EG-CBH2-1c/BGL, NBRC1440/ss-EG-CBH2-2c/BGL, and NBRC1440/ss-EG-CBH2-3c/BGL, which were cellulase secreting yeasts (Preparation Example 15) were inoculated into a fermentation medium containing 7.8 g/L of PSC, 10 g/L of yeast extract, 10 g/L of polypeptone, 50 mM of citrate buffer (pH 5.0), and 0.5 g/L potassium metabisulfite. The subsequent fermentation was performed anaerobically (dissolved oxygen level of about 0.05 ppm) at 30° C. At the beginning of fermentation, the cell concentration was adjusted to 75 g/L (wet cells). Since the amount of PSC added was 7.8 g/L, the theoretical yield of ethanol was 4.0 g/L. Measurement of ethanol concentration during fermentation was performed in the same manner as in Example 2.

Figure 9:
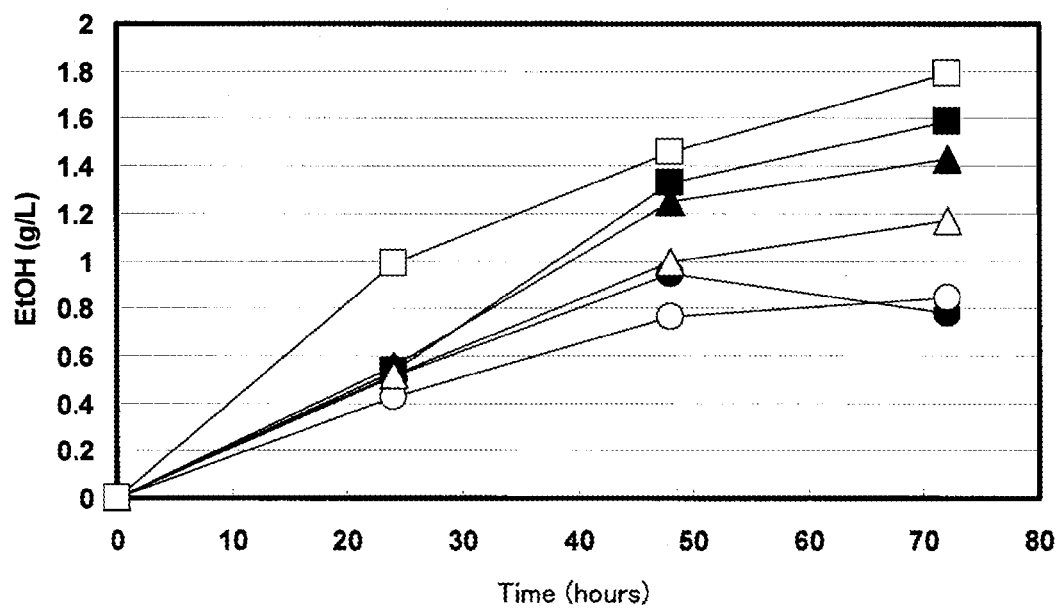
FIG. 9 is a graph showing the time course in amount of the ethanol production from phosphoric acid swollen cellulose (PSC) by cellulase surface-displaying yeasts and cellulase secreting yeasts.

FIG. 9 shows the results. FIG. 9 is a graph showing the time course in amount of the ethanol production from phosphoric acid swollen cellulose (PSC) by cellulase surface-displaying yeasts and cellulase secreting yeasts. The horizontal axis of the graph indicates the fermentation time (hours), and the vertical axis indicates the amount of ethanol produced (g/L). In the graph, the results for NBRC1440/ss-EG-CBH2-1c/BGL, NBRC1440/ss-EG-CBH2-2c/BGL, NBRC1440/ss-EG-CBH2-3c/BGL, NBRC1440/EG-CBH2-1c/BGL, NBRC1440/EG-CBH2-2c/BGL, and NBRC1440/EG-CBH2-3c/BGL are represented by black circle, black triangle, black square, white circle, white triangle, and white square, respectively.

It was demonstrated that, for either cellulase surface-displaying yeasts or cellulase secreting yeasts, the yield of ethanol fermentation from PSC is increased with the increased copy numbers of endoglucanase and cellobiohydrolase relative to one copy of β-glucosidase.

INDUSTRIAL APPLICABILITY

According to the present invention, an yeast for fermentation having an improved cellulose hydrolysis ability to enhance ethanol production can be obtained, which may result in efficient production of ethanol from cellulose-based materials, and thus leading to reduced cost. It is expected that the yeast can be applied to ethanol production from wastes such as soft biomass.

The invention claimed is:

1. A method for producing an yeast having an increased cellulose hydrolysis ability, comprising:
introducing a group of genes for enzymes capable of hydrolyzing cellulose into a noncellulolytic yeast to give a transformed yeast,
wherein the group of genes comprises a gene for an enzyme capable of hydrolyzing crystalline cellulose, a gene for an enzyme capable of hydrolyzing noncrystalline cellulose, and a gene for an enzyme capable of hydrolyzing cellobiose or cello-oligosaccharide,
wherein the integration copy number of each of the gene for the enzyme capable of hydrolyzing crystalline cellulose and the gene for the enzyme capable of hydrolyzing noncrystalline cellulose is at least two copies relative to one copy of the integration copy number of the gene for the enzyme capable of hydrolyzing cellobiose or cello-oligosaccharide.

2. The method according to claim 1, wherein the enzyme capable of hydrolyzing crystalline cellulose is cellobiohydrolase and the enzyme capable of hydrolyzing noncrystalline cellulose is endoglucanase.

3. The method according to claim 1, wherein the introduction into the noncellulolytic yeast is performed such that at least one of the enzyme capable of hydrolyzing crystalline cellulose and the enzyme capable of hydrolyzing noncrystalline cellulose is surface-displayed.

4. The method according to claim 1, wherein the enzyme capable of hydrolyzing cellobiose or cello-oligosaccharide is β-glucosidase.

5. The method according to claim 1, wherein the introduction into the noncellulolytic yeast is performed such that the enzyme capable of hydrolyzing cellobiose or cello-oligosaccharide is surface-displayed.

6. The method according to claim 2, wherein the introduction into the noncellulolytic yeast is performed such that at least one of the enzyme capable of hydrolyzing crystalline cellulose and the enzyme capable of hydrolyzing noncrystalline cellulose is surface-displayed.

7. The method according to claim 4, wherein the introduction into the noncellulolytic yeast is performed such that the enzyme capable of hydrolyzing cellobiose or cello-oligosaccharide is surface-displayed.

* * * * *